(12) United States Patent
Macomber et al.

(10) Patent No.: US 8,215,186 B2
(45) Date of Patent: Jul. 10, 2012

(54) LOWER-LIMB PROSTHESIS FORCE AND MOMENT TRANSDUCER

(75) Inventors: Ben Gilbert Macomber, Shoreline, WA (US); David Alan Boone, Seattle, WA (US); James Christian Beck, Missoula, MT (US)

(73) Assignee: Orthocare Innovations LLC, Oklahoma City, OK (US)

( * ) Notice: Subject to any disclaimer, the term of this patent is extended or adjusted under 35 U.S.C. 154(b) by 0 days.

(21) Appl. No.: 12/986,024

(22) Filed: Jan. 6, 2011

(65) Prior Publication Data
US 2011/0130684 A1 Jun. 2, 2011

Related U.S. Application Data

(63) Continuation of application No. 11/853,707, filed on Sep. 11, 2007, now Pat. No. 7,886,618.

(60) Provisional application No. 60/843,810, filed on Sep. 11, 2006.

(51) Int. Cl.
*G01L 1/22* (2006.01)
(52) U.S. Cl. .................................. 73/862.044
(58) Field of Classification Search .............................. 73/862.041–862.046
See application file for complete search history.

(56) References Cited

U.S. PATENT DOCUMENTS

| 4,640,138 | A | | 2/1987 | Meyer |
| 4,911,023 | A | | 3/1990 | Izumi |
| 5,127,420 | A | | 7/1992 | Horvath |
| 5,197,488 | A | * | 3/1993 | Kovacevic ..................... 600/595 |
| 5,253,656 | A | * | 10/1993 | Rincoe et al. ................. 600/595 |
| 5,360,016 | A | | 11/1994 | Kovacevic |
| 5,413,611 | A | * | 5/1995 | Haslam et al. .................. 623/25 |
| 5,800,565 | A | | 9/1998 | Biedermann |
| 5,880,976 | A | | 3/1999 | DiGioia, III |
| 5,955,667 | A | | 9/1999 | Fyfe |
| 5,993,400 | A | * | 11/1999 | Rincoe et al. ................. 600/595 |
| 5,995,738 | A | | 11/1999 | DiGioia, III |

(Continued)

FOREIGN PATENT DOCUMENTS

DE  3701372 A1  7/1988

(Continued)

OTHER PUBLICATIONS

Bibliography with communication provided by an inventor of present U.S. Appl. No. 11/853,707 to a Third Party, Sep. 3, 2008, 6 pages.

(Continued)

*Primary Examiner* — Max Noori
(74) *Attorney, Agent, or Firm* — Christensen O'Connor Johnson Kindness PLLC

(57) ABSTRACT

A computerized prosthesis alignment system includes a transducer that can measure socket reactions in the anterior/posterior plane and the right/left planes, while canceling or reducing the transverse forces on the measurements of these socket reactions. In addition, the transducer is also capable of determining the axial load or weight experienced by the prosthesis. The computerized prosthesis alignment system is in communication with a host computer. The moment data from the transducer is interpreted by the user via a computer interface. The host computer includes memory for storing one or more applications. These applications receive data from the transducer, interpret the data with discrete algebraic or fuzzy logic algorithms, and display the output numerically and graphically. Applications may also interpret the data to provide analyses to the user for aligning the prosthesis.

34 Claims, 31 Drawing Sheets

U.S. PATENT DOCUMENTS

| | | | |
|---|---|---|---|
| 6,301,964 B1 | 10/2001 | Fyfe | |
| 6,513,381 B2 | 2/2003 | Fyfe | |
| 6,821,299 B2 * | 11/2004 | Kirking et al. | 623/20.14 |
| 6,831,603 B2 | 12/2004 | Menache | |
| 7,150,762 B2 | 12/2006 | Caspers | |
| 7,381,223 B2 | 6/2008 | Kovacevic | |
| 7,886,618 B2 | 2/2011 | Macomber | |
| 2003/0069644 A1 | 4/2003 | Kovacevic | |
| 2004/0059433 A1 | 3/2004 | Slemker | |
| 2005/0010139 A1 | 1/2005 | Aminian | |
| 2005/0166685 A1 | 8/2005 | Boiten | |
| 2005/0267600 A1 | 12/2005 | Haberman | |
| 2006/0135883 A1 | 6/2006 | Jónsson | |
| 2006/0195197 A1 | 8/2006 | Clausen | |
| 2006/0206214 A1 | 9/2006 | Clausen | |
| 2008/0140221 A1 | 6/2008 | Macomber | |
| 2008/0276725 A1 | 11/2008 | Pusch | |

FOREIGN PATENT DOCUMENTS

| | | |
|---|---|---|
| DE | 9408556 U1 | 7/1994 |
| DE | 10 2005 051 496 A1 | 5/2007 |
| EP | 0449799 A1 | 10/1991 |
| RU | 2039538 C1 | 7/1995 |
| WO | 9531949 A2 | 11/1995 |
| WO | 0172245 A2 | 10/2001 |
| WO | 2007048374 A1 | 5/2007 |
| WO | 2007048375 A1 | 5/2007 |
| WO | 2007048404 A2 | 5/2007 |
| WO | 2008033852 A2 | 3/2008 |

OTHER PUBLICATIONS

Blumentritt, S., "A New Biomechanical Method for Determination of Static Prosthetic Alignment," Prosthetics and Orthotics International 21(2):107-113, Aug. 1997.

Boone, D., and M. Zhang, "PR 5D7.09—Computerized Prosthesis Alignment Instrument," Proceedings of the 11th World Congress of the International Society for Prosthetics & Orthotics, Aug. 1-6, 2004, Hong Kong, p. 322.

Boone, D., and M. Zhang, "FP 5E4.5—Determination of Prosthetic Malalignment by Fuzzy-Logic Algorithm," Proceedings of the 11th World Congress of the International Society for Prosthetics & Orthotics, Aug. 1-6, 2004, Hong Kong, p. 363.

Chahande, A.I., et al., "Neural Network Models for Customized Alignment of Endoskeleton BK Prosthesis," Neural Networks: IEEE World Congress on Computational Intelligence 6:3507-3511, Orlando, Fla., Jun. 27-Jul. 2, 1994.

Frossard, L., et al., "Development of Preliminary Testing of a Device for the Direct Measurement of Forces and Moments in the Prosthetic Limb of Transfemoral Amputees During Activities of Daily Living," Journal of Prosthetics and Orthotics 15(4):135-142, 2003.

Gusdal, D., et al., "Force Transducer to Assist With Lower Limb Prosthetic Alignment," <http://www.rehab.research.va.gov/prog/99/99prch01.htm> [retrieved Jul. 6, 2009], 2 pages.

Hansen, A., et al., "Automated Alignment System for Prosthetic Feet," Northwestern University Technology Transfer Program, © 2001, <http://www.northwestern.edu/ttp/technology/abstracts/20030.html> [retrieved May 13, 2002], 2 pages.

Jones, D., and J.P. Paul, "Analysis of Variability in Pylon Transducer Signals," Prostethics and Orthotics International 2:161-166, 1978.

Macomber, B., and D.A. Boone, "Method for Aligning a Prosthesis," U.S. Appl. No. 11/853,711, filed Sep. 11, 2007.

Mizrahi, J., et al., "Alignment Procedure for the Optimal Fitting of Lower Limb Prostheses," Journal of Biomedical Engineering 8(3):229-234, Jul. 1986.

Naumann, S., et al., "Dynamic Prosthetic Alignment Assistant," <http://www.rehab.research.va.gov/prog/99/99prch01.htm> [retrieved Jul. 6, 2009], 2 pages.

Nietert, M., et al., "Loads in Hip Disarticulation Prostheses During Normal Daily Use," Prosthetics and Orthotics International 22:199-215, 1998.

Notification of Transmittal of International search Report and the Written Opinion of the International Searching Authority mailed Nov. 4, 2009, in related International Application No. PCT/US2009/050428, filed Jul. 13, 2009.

Office Action mailed Oct. 19, 2009, in related U.S. Appl. No. 11/853,711, filed Sep. 11, 2007.

Parker, K., et al., "Effects of Trans-Tibial Amputee Alignment Changes on Dynamic Socket Loads," Gait and Posture 9(2):135-136, 1999.

Reed, R.D., et al., "Neural Network Aided Prosthetic Alignment," IEEE International Conference on Systems, Man and Cybernetics: Intelligent Systems for the 21st Century, Vancouver, BC, Canada, Oct. 22-25, 1995, pp. 505-508.

Sanders, J.E., et al., "A Measurement Device to Assist Amputee Prosthetic Fitting," Journal of Clinical Engineering 19(1):63-70, Jan./Feb. 1994.

Sanders, J.E., et al., "A Modular Six-Directional Force Sensor for Prosthetic Assessment: A Technical Note," Journal of Rehabilitation Research and Development 34(2):195-202, Apr. 1997.

Sanders, J.E., et al., "A Portable Measurement System for Prosthetic Triaxial Force Transducers," IEEE Transactions on Rehabilitation Engineering 3(4):366-372, Dec. 1995.

Sanders, J.E., et al., "Changes in Interface Pressures and Shear Stresses Over Time on Trans-Tibial Amputee Subjects Ambulating With Prosthetic Limbs: Comparison of Diurnal and Six-Month Differences," Journal of Biomechanics 38:1566-1573, 2005.

Sanders, J.E., et al., "Computer-Aided Prosthetic Alignment for Lower-Limb Amputees," Proceedings of the 15th Annual International Conference of the IEEE Engineering in Medicine and Biology Society, San Diego, Calif., Oct. 28-31, 1993, pp. 1282-1283.

Sanders, J.E., et al., "Dynamic Alignment of a Lower-Limb Prosthesis by Computational Analysis of Gait Force-Time Data," Proceedings, Eighth Biennial Conference, Canadian Society for Biomechanics, Calgary, AB, Canada, Aug. 18-20, 1994, pp. 50-51.

Seliktar, R., "Computer Aided Dynamic Alignment of Below Knee Prostheses," in J. Raviv (ed.) "Proceedings of the IFIP-IMIA Working Conference on Uses of Computers in Aiding the Disabled: Haifa, Israel, Nov. 3-5, 1981," North Holland Publishing Company, New York, 1982, pp. 87-97.

Third Party communications (e-mail)and letter) to Applicant (dated Aug. 21, 2008) and Applicant's attorney (dated Feb. 20, 2009) relating to references known to Third Party, 3 pages.

Winarski, D.J, and J.R. Pearson, "Analytical Description of Minimum Energy Expenditure Surfaces," Journal of Biomechanical Engineering, 110:386-391, Nov. 1988.

Berme, N., et al., "A Shorter Pylon Transducer for Measurement of Prosthetic Forces and Moments During Amputee Gait," Engineering in Medicine 4(4):6-8, Oct. 1975.

Sanders, J.E., "Ambulation With a Prosthetic Limb: Mechanical Stresses in Amputated Limb Tissues," doctoral dissertation, University of Washington, Seattle, Washington, 1991, 362 pages.

Sanders, J.E., and Daly, C.H., "Measurement of Stresses in Three Orthogonal Directions at the Residual Limb-Prosthetic Socket Interface," IEEE Transactions on Rehabilitation Engineering 1(2):79-85, Jun. 1993.

Request for Ex Parte Reexamination filed Mar. 1, 2012, in U.S. Appl. No. 90/012,170, which is an Ex Parte Reexamination of U.S. Patent No. 7,886,618, 24 pages.

Order Granting Request for Ex Parte Reexamination mailed Apr. 3, 2012, in U.S. Appl. No. 90/012,170, filed Mar. 1, 2012, which is an Ex Parte Reexamination of U.S. Patent No. 7,886,618, 17 pages.

* cited by examiner

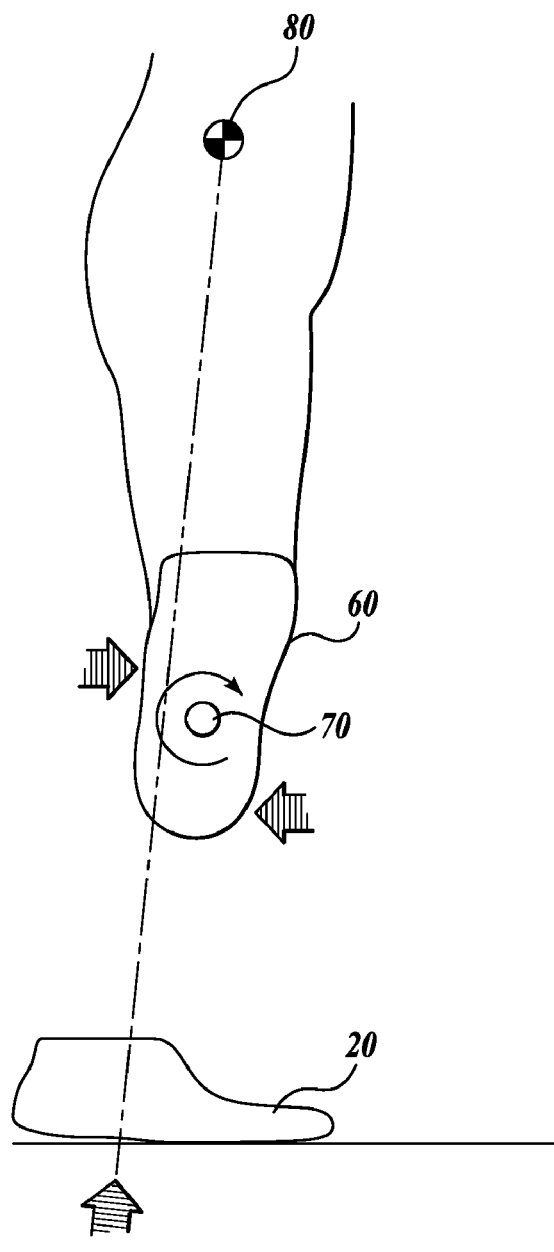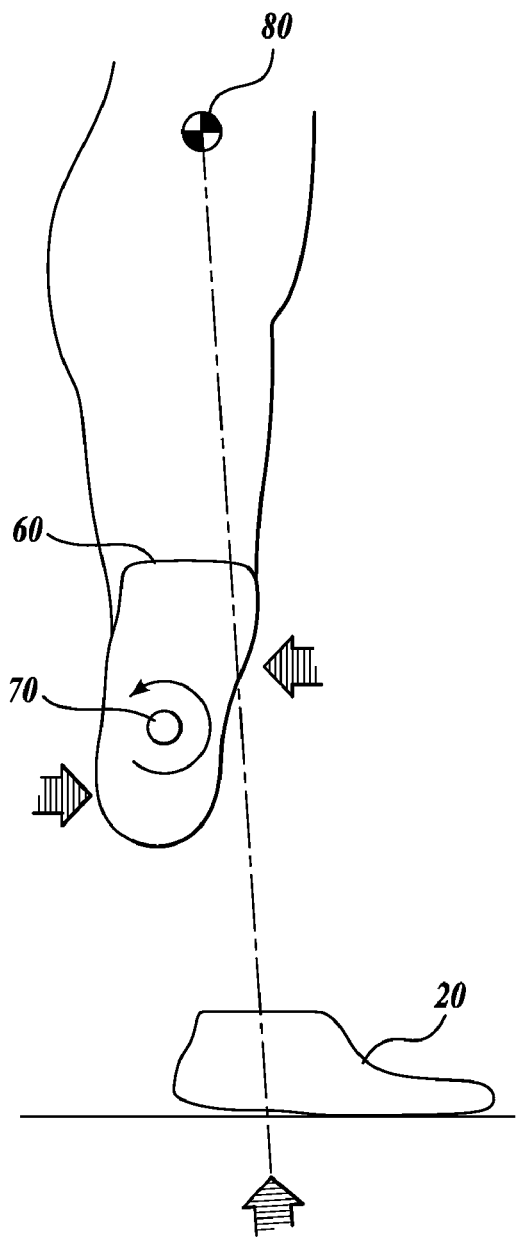
*Fig.2A.*  *Fig.2B.*

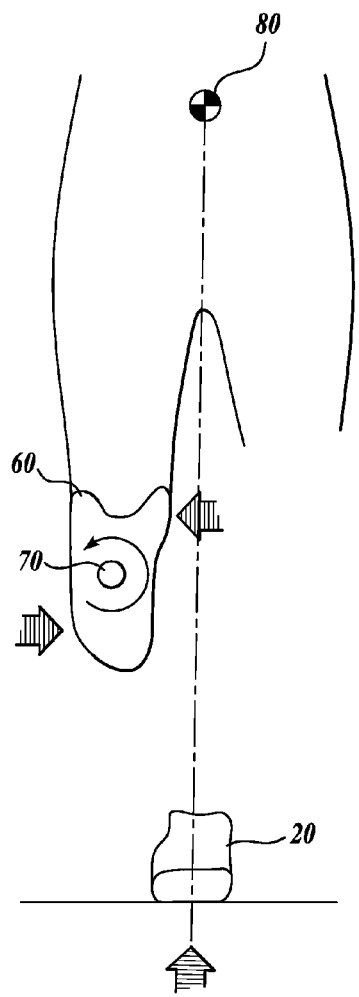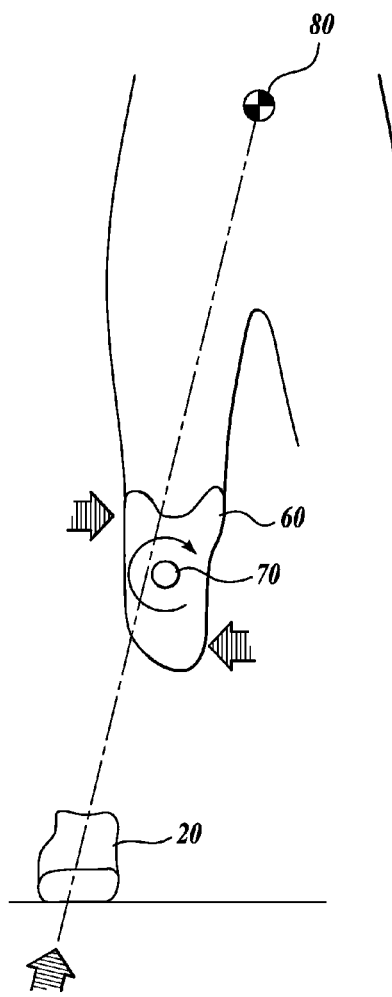
*Fig.3A.*    *Fig.3B.*

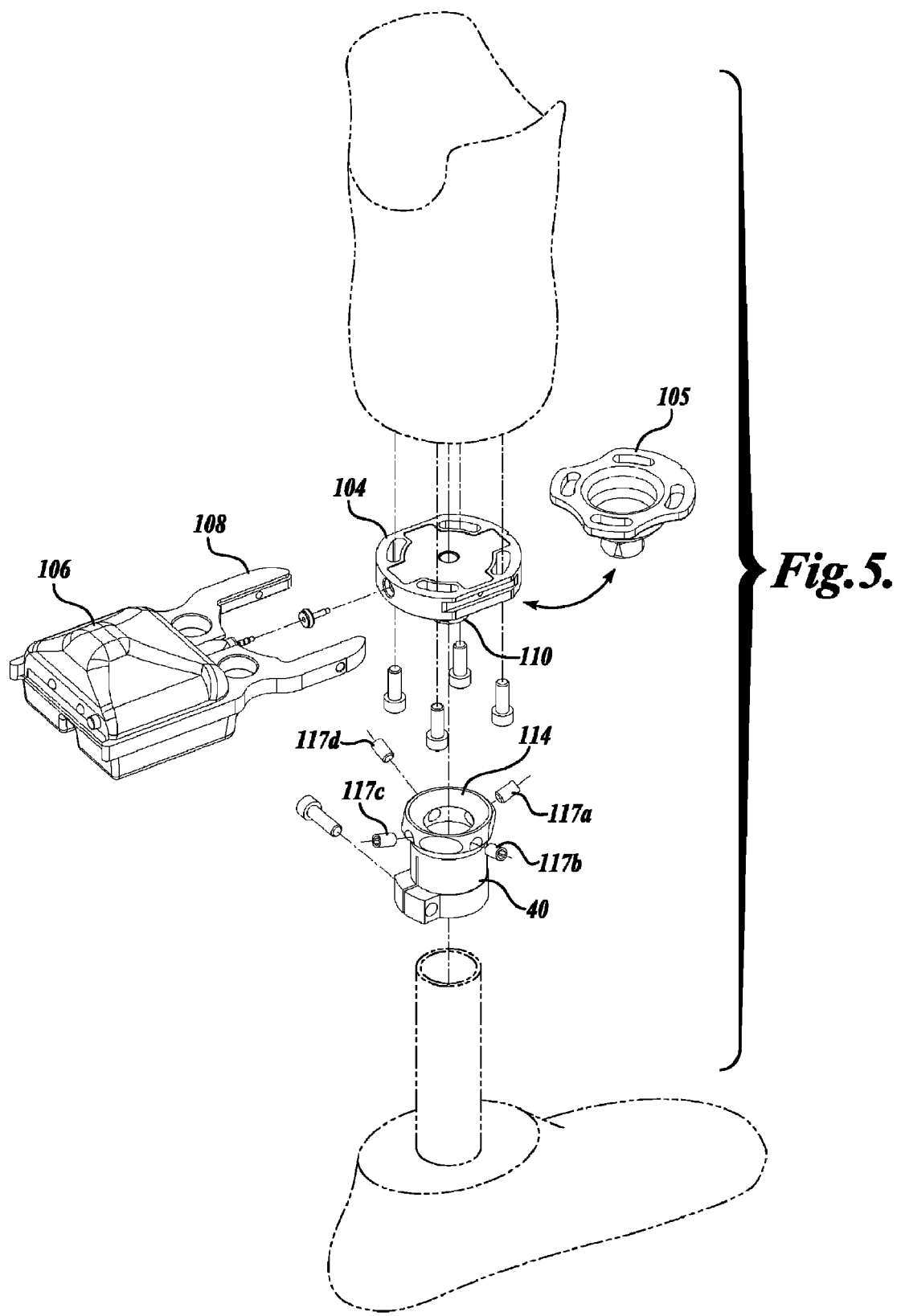

LOWER-LIMB PROSTHESIS FORCE AND MOMENT TRANSDUCER

CROSS-REFERENCE(S) TO RELATED APPLICATIONS

This application is a continuation of U.S. patent application Ser. No. 11/853,707, filed Sep. 11, 2007, which claims the benefit of U.S. Provisional Application No. 60/843,810, filed Sep. 11, 2006, both of which applications are expressly incorporated herein by reference in their entirety.

STATEMENT OF GOVERNMENT LICENSE RIGHTS

This invention was made with Government support under Grant No. 4 R44 HD47119-20 awarded by the National Institutes of Health. The U.S. Government has certain rights in the invention.

BACKGROUND

Alignment of a prosthesis is an important element of optimizing its function. FIG. 1 illustrates a representative prosthesis for a transtibial amputee. The prosthesis 10 includes a foot portion 20 rigidly, but adjustably, affixed to a pylon 30. The pylon 30, in turn, is connected to the prosthesis socket 60 via a tube clamp adaptor 40 and a pyramid adaptor 50. The connection between the tube clamp adaptor 40 and the prosthesis socket 60 is adjustable to fix the alignment. Although not shown, the tube clamp adaptor 40 has an concave spherical, load-bearing surface on the upper end of the tube clamp adaptor 40. This surface includes a central hole through which the tube clamp adaptor 40 receives the pyramid adaptor 50. The pyramid adaptor 50 is so named because of the inverted pyramid-shaped protuberance that fits into the central hole of the surface in the tube clamp adaptor 40. The pyramid adaptor 50 has a convex spherical load-bearing surface designed to be supported by the concave spherical surface on the tube clamp adaptor 40 that allows articulation in directions relative to the horizontal plane. In terms familiar to aviation, these are "pitch" and "roll." Thus, the pyramid adaptor 50 can be oriented in any configuration in the anterior/posterior plane, as well as the right/left plane. The pyramid adaptor 50 is locked in place by tightening four set screws (not shown) that press against the respective four sides of the inverted pyramid. The pyramid adaptor 50 further has an upper flange that rigidly attaches to the underside of the prosthesis socket 60. In a prosthesis, the alignment of the socket 60 and pylon 30 affects the functional performance and comfort of the person by altering the manner in which the weight-bearing load is transferred between the amputated limb and the ground.

The importance of alignment has been recognized for many decades, but little progress has been made to give a prosthetist the tools needed to optimize this aspect of prosthetic care. Until now, prosthesis alignment has been an imprecise and inconsistent practice based primarily on the subjective opinion and the experience of the prosthetist to visually determine the proper alignment.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In order to assist a prosthetist to optimally align a prosthesis, a computerized prosthesis alignment system is provided that can directly measure prosthesis socket reactions with a transducer integrated into the prosthesis. "Socket reactions" refer to moments experienced at the prosthesis socket 60 in the anterior/posterior plane and the right/left plane. Another moment is experienced by the prosthesis socket 60, but which is not generally needed for the alignment of the prosthesis, is the transverse force (i.e., force that tends to rotate the socket 60 in the horizontal plane). Again, in aviation terms, this force would induce motion referred to as "yaw."

The computerized prosthesis alignment system includes a transducer that can measure the socket reactions in the anterior/posterior plane and the right/left planes, while canceling or reducing the transverse forces on the measurements of these socket reactions. In addition, the transducer is also capable of determining the axial load or weight experienced by the prosthesis.

The transducer is a modified pyramid adaptor that includes strain gages positioned along anterior and posterior beams and right and left beams that enable measuring the anterior/posterior moment and the right/left moment, while canceling or reducing the transverse moments. The beams support the inverted pyramid, so that the forces on the pyramid are directly borne by the beams. A hat substantially configured to match the concave spherical surface of the tube clamp adaptor 40 is placed over the beams to bear the axial load.

The computerized prosthesis alignment system further includes a master unit coupled to the transducer to enable wireless transmission of data to a host computer for processing and display of the data and also for providing instructions for aligning the prosthesis based on the data. The master unit includes a bracket to couple the master unit to the transducer. The master unit includes a power source, a microprocessor system, a serial communications bus, a serial to peripheral communications bus, a gyroscope, a laser line generator, a wireless communications modem, and various indicator lamps and switches to enable the methods of aligning a prosthesis.

The computerized prosthesis alignment system is in communication with a host computer. The moment data from the transducer is interpreted by the user via a computer interface. The host computer includes memory for storing one or more applications. These applications are for receiving data from the transducer, interpreting the data with discrete algebraic or fuzzy logic algorithms, and displaying the output numerically and graphically. Applications may also interpret the data to provide analyses to the user for aligning the prosthesis. The one or more applications detect the onset and cessation of walking movements, identify and enumerate gait cycles by the transitions between weight bearing and non-weight bearing actions on the transducer, index the start and end of the stance phase of each gait cycle, mathematically interpolate the data to discrete increments of stance, calculate variables used as force moment descriptors of each resulting force and moment waveform, label and save the stance phase normalized curves and variables, interpret the variable values by means of algorithms to search for optimal values and patterns determined a priori. These applications also provide a graphical user interface for initialization, orientation, numerical analysis, graphical display, alignment analysis, and digital recording of transducer data. Data may be displayed as line charts, histograms, or numerical values. Sampled data may be compared to expected or theoretically optimal output.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 2A and 2B are diagrammatical illustrations of the moments experienced by a prosthesis in the anterior/posterior plane;

FIGS. 3A and 3B are diagrammatical illustrations of the moments experienced by a prosthesis in the right/left plane;

FIG. 5 is a diagrammatical illustration of an exploded view of the computerized prosthesis alignment system of FIG. 4;

DETAILED DESCRIPTION

FIGS. 2A, 2B, 3A, and 3B are intended to illustrate the moments experienced at the prosthesis socket 60 that affect the comfort and function of the prosthesis. Moments are induced at the socket 60, generally when there are unbalanced forces acting on opposite sides of a theoretical reference point 70 of the socket 60. For example, the more the foot 20 is behind the center of rotation 70, the more that a clockwise moment in the anterior/posterior plane is experienced at the socket 60. On the other hand, if the foot 20 is moved forward of the reference point 70, a counterclockwise moment in the anterior/posterior plane is experienced at the socket 60. Similar forces can be experienced in the right/left plane.

For example, referring to FIGS. 3A and 3B, the more the foot 20 is moved to the left of the reference point 70, the more a counterclockwise moment in the right/left plane is experienced at the socket 60. On the other hand, if the foot 20 is moved to the right of the reference point 70, a clockwise moment in the right/left plane is experienced at the socket 60.

These moments or socket reactions relate to what the amputee feels and the prosthetist visually notices when dynamically aligning the prosthesis. Using the computerized prosthesis alignment system as described herein, the prosthetist can gain input that is even more sensitive than the trained eye. The computerized prosthesis alignment system continuously measures the moments while the amputee is walking. The computerized prosthesis alignment system includes hardware and software to automatically measure and interpret the relevant moment information from a series of steps and provides prosthesis-specific gait analysis. In one embodiment, for example, the moment information is compared to a stored optimal model of alignment. A gait analysis application is provided that compares the real time moment information with the model of alignment and provides feedback on how the prosthesis can be aligned to move closer to the model. Feedback to the prosthetist is presented in concise and easy-to-understand language and graphs. In one embodiment, instructions are provided by the computerized prosthesis alignment system for adjusting the pyramid adaptor alignment screws in simple and explicit terms.

Figure 1:
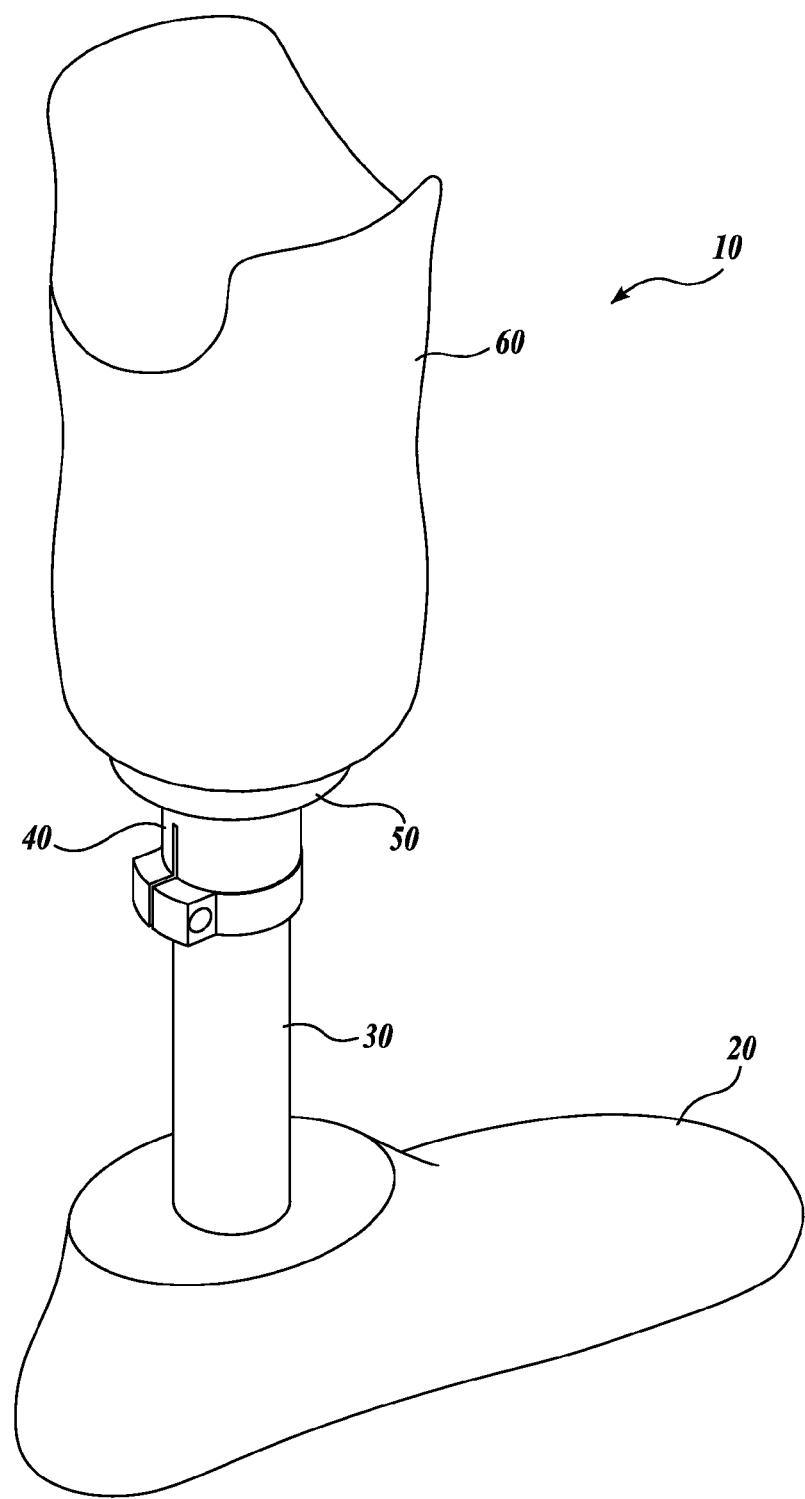
FIG. 1 is a diagrammatical illustration of a prior art prosthesis.
Figure 4:
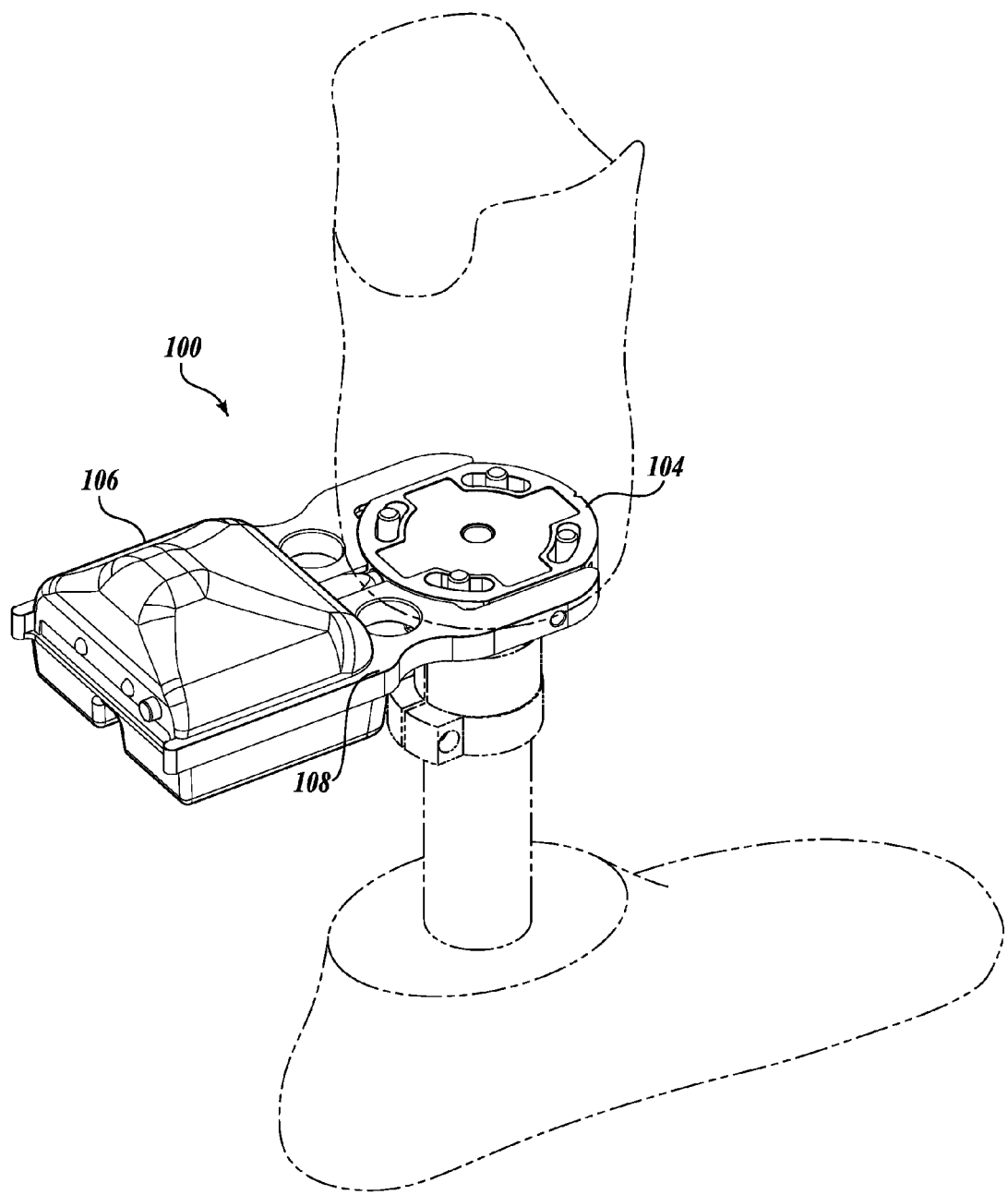
FIG. 4 is a diagrammatical illustration of a computerized prosthesis alignment system in accordance with an embodiment of the present invention incorporated into a prosthesis.

Referring to FIGS. 4 and 5, the computerized prosthesis alignment system 100 hardware is shown integrated into a prosthesis (shown in phantom lines). The computerized prosthesis alignment system 100 includes a transducer 104 (or modified pyramid adaptor) and a master unit 106. A bracket 108 supports the master unit 106 and is used to connect the master unit 106 to the transducer 104 in a rigid but removable manner. The computerized prosthesis alignment system software will be described below in the context of applications. For ease of understanding, the use of the computerized prosthesis alignment system 100 will be described in association with a prosthetic limb specific for a transtibial prosthesis. However, it is to be appreciated that the computerized prosthesis alignment system 100 may be used for other prosthesis and/or in other fields of use besides prosthesis alignment, such as orthopedics.

The transducer 104 aids, quantifies, and records prosthesis alignment adjustments with software applications on a host computer in wireless radio communication with the transducer 104.

In accordance with one embodiment, the transducer 104 includes a first major side and a second major side. The first and second major sides, respectively, may face upwards and downwards in the prosthesis. For purposes of illustrating one embodiment, the major side of the transducer 104 facing down includes an inverted pyramid 110. The inverted pyramid 110 is a standard in the industry. In general, the inverted pyramid resembles a partial, 4-sided pyramid, wherein the surface of each side is at an angle relative to a plane perpendicular to the longitudinal axis of the inverted pyramid so that each side hangs over the base of the "pyramid." The inverted pyramid 110 fits into the central hole of the tube clamp adaptor 40. As described in the Background Section, the tube clamp adaptor 40 includes a concave spherical surface 114 on the upper end thereof. Four set screws 117a, 117b, 117c, 117d used for fixing the position and, thus, the alignment of the prosthesis socket 60 are provided that correspond to each side surface of the inverted pyramid 110. The four set screws 117a, 117b, 117c, 117d are threaded and pass through the tube clamp adaptor 40 so as to press against the corresponding surface of the inverted pyramid 110, thus providing a rigid but adjustable alignment. The tube clamp adaptor 40 includes a concave spherical surface 114 and the transducer 104 includes a corresponding convex hat 120 as load-bearing surfaces so that the alignment between the tube clamp adaptor 40 and the transducer 104 may be adjusted in the anterior/ posterior plane and the right/left plane. While the transducer 104 can be articulated in the anterior/posterior and right/left planes, rotation of the inverted pyramid 110 and transducer 104 with respect to the tube clamp adaptor 40 is prevented due to the flat-sided surfaces of the inverted pyramid 110 engaging the ends of the set screws 117a, 117b, 117c, and 117d.

Figure 6A:
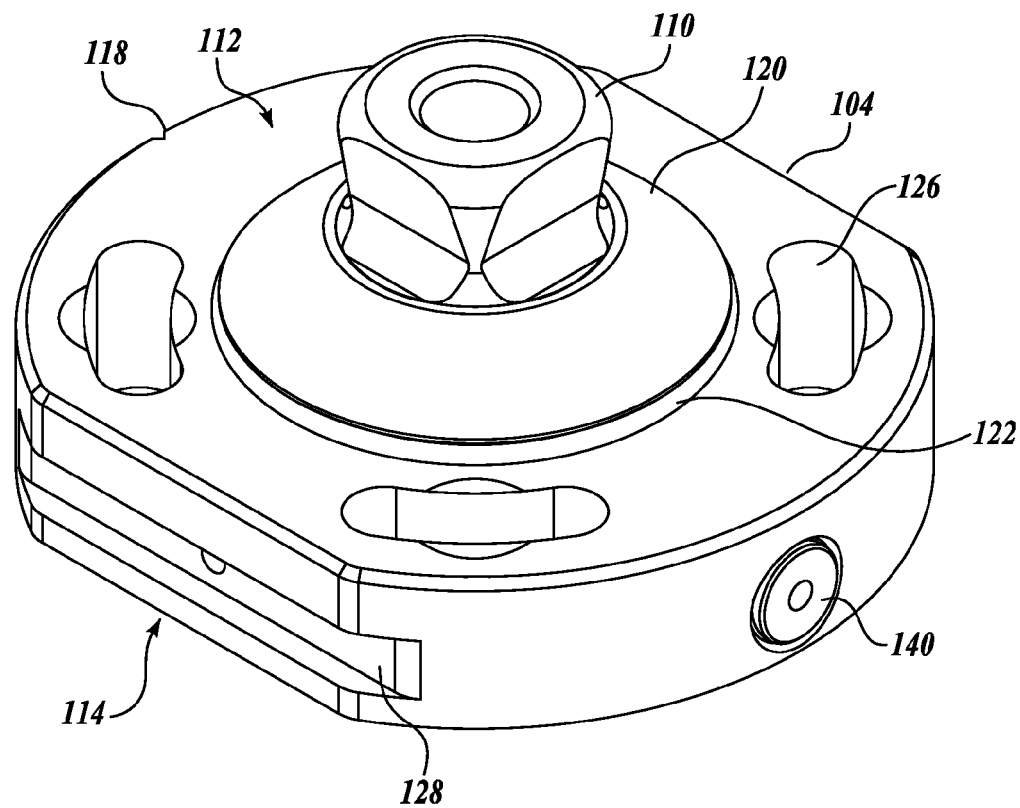
FIG. 6A is a diagrammatical illustration of a transducer in accordance with an embodiment of the present invention.
Figure 6B:
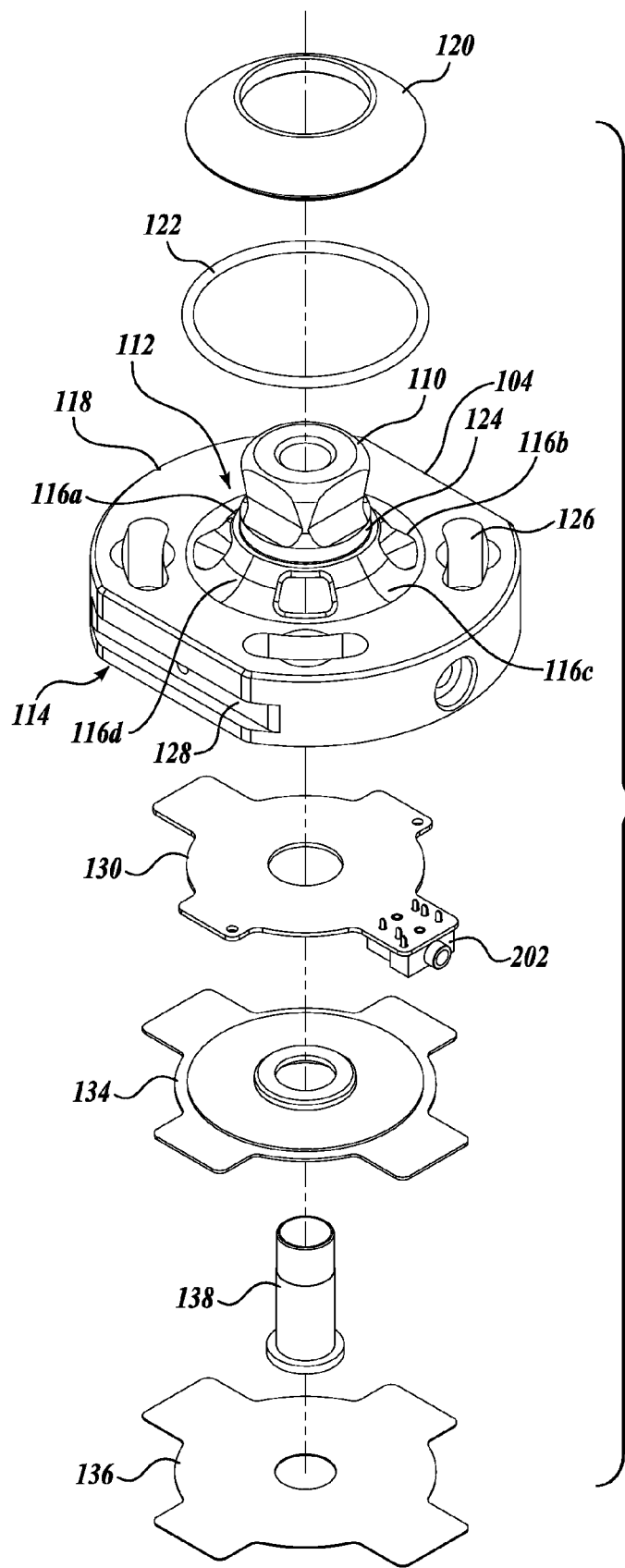
FIG. 6B is a diagrammatical illustration of an exploded view of the transducer of FIG. 6A.

As best seen in FIGS. 6A and 6B, wherein the transducer 104 has been inverted for clarity, the transducer 104 includes a body having the first major side 112 and the second major side 114. For purposes of rotationally aligning the transducer 104 with the prosthesis socket 60, an anterior marking notch 118 is provided, the function of which will be discussed below. The major side 112 supports the inverted pyramid 110. In the illustration of FIGS. 6A and 6B, the inverted pyramid 110 is pointed up; however, the transducer 104 can be used in an up or down configuration, depending on the configuration of the prosthesis. As best seen in FIG. 6B, the body of the transducer 104 on the major side 112 supporting the inverted pyramid 110 slopes upwards to support the inverted pyramid 110. The body of the transducer 104 includes apertures separating the major side 112 from the inverted pyramid 110. Between adjacent apertures, a beam is provided that extends from the major surface 112 to the inverted pyramid 110. Four beams 116a, 116b, 116c, and 116d are provided that extend from the major side 112 of the transducer 104 to the inverted pyramid 110. The arrangement of beams 116a, 116b, 116c, and 116d produces a cruciform structure. The beams 116a, 116b, 116c, and 116d each support a side of the inverted pyramid 110. There is an anterior beam 116a for supporting the anterior side of the inverted pyramid 110, a posterior beam 116c for supporting the posterior side of the inverted pyramid 110, a left beam 116b for supporting the left side of the inverted pyramid 110, and a right beam 116d for supporting the right side of the inverted pyramid 110. For purposes of clarity, the convention as to the right and left side is maintained from FIG. 5. As will be described further below, the beams 116a-d are able to transfer the moments acting on the prosthesis socket 60 to the transducer 104 to thereby measure the anterior/posterior moment and the right/left moment. To this end, strain gages 118 are positioned on each side of each beam 116a, 116b, 116c, and 116d within the adjacent apertures.

Figure 7:
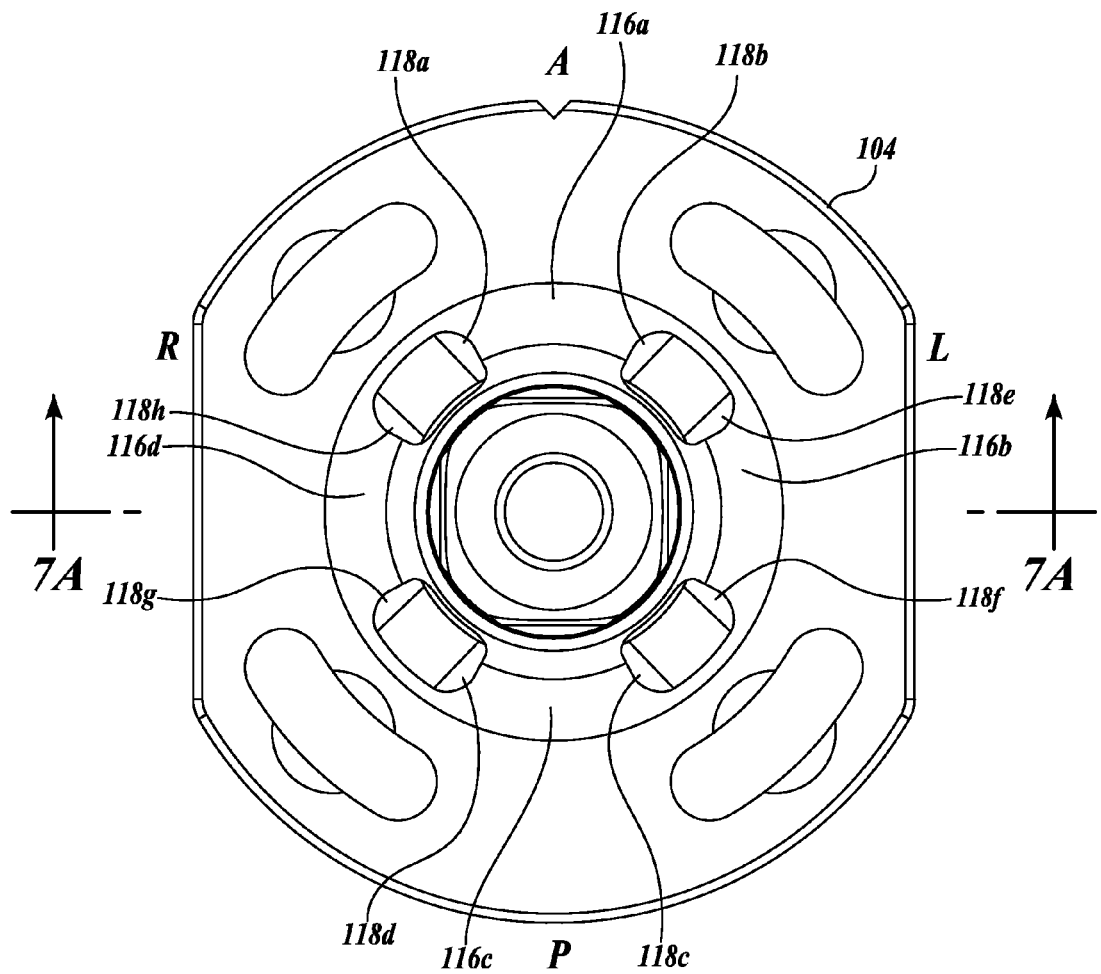
FIG. 7 is a diagrammatical illustration of a bottom view of the transducer of FIG. 6A.

As best seen in FIG. 7, the anterior beam 116a includes a first 118a (anterior-right) and second 118b (anterior-left) strain gage attached to each side surface of the beam 116a. The posterior beam 116c includes a third 118c (posterior-left) and fourth 118d (posterior-right) strain gage attached to each side surface of the posterior beam 116c. The left beam 116b includes a fifth 118e (left-anterior) and sixth 118f (left-posterior) strain gage attached to each side surface of the left beam 116b. The right beam 116d includes a seventh 118g (right-posterior) and eighth 118h (right-anterior) strain gage attached to each side surface of the right beam 116d. Two sets of four strain gages 118a-h are arranged into two balanced bridges, each with a passive/resistive temperature compensation component in series with each bridge so as to develop a voltage representative of the total bridge resistance. This voltage signal is a measure of the axial force. The orientation of the balanced bridges allows for calculation of moments in two orthogonal planes. The strain gages 118a-h can be semiconductor or foil strain gages. Semiconductor strain gages are preferred for their small size and superior gage factor, enabling a more rigid, stronger, more sensitive and more compact design than other types of strain gage. Titanium alloys, such as TI-6AL-4V, are preferable for their strength, good spring properties, and relatively low coefficient of thermal expansion. One embodiment of a suitable strain gage is manufactured by Micron Instruments of Simi Valley, Calif., under the Model No. SS-060-033-500P. This semiconductor strain gage is made from "p" doped bulk silicon. The strain gages are reported to have an operating strain of ±2000μ inch/inch and ±3,000μ inch/inch maximum. The linearity is reported to be better than ±0.25% to 600±μ inch/inch and better than ±1.5% to 1,500±μ inch/inch. The no-load resistance of the strain gage is reported at approximately 540±50 ohms at 78° F. The gage factor is reported to be 140±10.

Figure 7A:
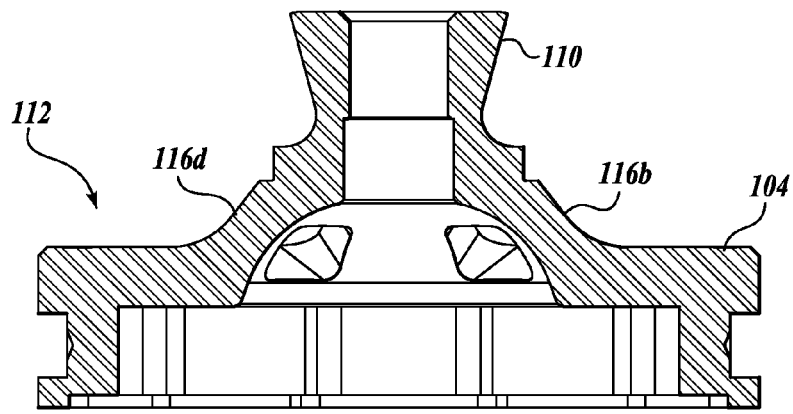
FIG. 7A is a diagrammatical illustration of a cross-sectional view of the transducer of FIG. 6A.

FIG. 7A is a cross-sectional illustration of the transducer 104 of FIG. 7. The left beam 116b and the right beam 116d are visible supporting the inverted pyramid 110 from the base. The beams 116b and 116d are formed from and rise from the major side 112 of the transducer 104. The beams 116a-d raise the inverted pyramid 110 above the surface of major side 112 of the transducer 104.

Referring back to FIG. 6B, a load-bearing hat 120 having a convex spherical surface to match with the tube clamp adaptor 40 is placed over the beams 116a-d. The upper inner diameter of the hat 120 rests on a lip 124 below the inverted pyramid 110 and above the individual beams 116a-d. The body of the hat 120 being clamped between the tube clamp adaptor 40 and the inverted pyramid 110, transfers the prosthesis socket 60 reaction forces to the beams 116a-d, including the anterior/posterior and right/left moments. An O-ring seal 122 placed between the hat 120 and the major side 112 prevents dirt and other contamination from entering the inside of the transducer 104 that houses the electronic components. The transverse moments can be canceled, or at least reduced, by arranging the strain gages so that a transverse moment sensed by any strain gage is canceled by an oppositely placed strain gage. The beams 116a-d being joined to the inverted pyramid 110 that, in turn, is in contact with the four set screws 117a-d permits the transfer of the anterior/posterior moment and right/left moment to the beams 116a-d. Any anterior and/or posterior moment and any right and/or left moment are transferred from the inverted pyramid 110 to the beams 116-116d wherein the stresses (compression and tension) are sensed by the strain gages 118a-h. The arrangement of strain gages 118a, 118b, 118c, 118d, 118e, 118e, 118f, 118g, and 118h allows differentiation between anterior/posterior and right/left directions of the moments and cancels transverse plane moments. The load-bearing hat 120 receives the axial force or weight and transfers the weight onto the lip 124 above the beams. The beams 116a, 116b, 116c, and 116d receive the axial force and respond by compressing, which is sensed by the strain gages 118a, 118b, 118c, 118d, 118e, 118f, 118g, and 118h.

In an alternate embodiment, strain gages 118a-118h may be combined differently or switched electrically with electronic switching elements, such as analog switches, into circuit patterns sensitive to moments in the transverse plane while rejecting moments in the other orthogonal planes. For example, if strain gages 118d and 118a are swapped, anterior/posterior moments would be substantially rejected and transverse moments about the axis of the transducer 104 would be sensed. In an embodiment wherein electronic switching of the strain gages' combination is employed, the transducer 104 may be dynamically reconfigured by software to selectively sense or reject moments in any of the three orthogonal planes. Other embodiments may employ circuits other than the Wheatstone bridge arrangement shown in FIG. 9. For example, each strain gage may be part of a simple voltage divider network. In this embodiment, the voltage resulting across the strain gage would be amplified and converted to a digital value as described below. This scheme allows capture of raw data representative of moments in all three planes, axial and shear forces, all concurrently and without the need to reconfigure bridge circuits, requiring software to combine and analyze the values from each strain gage.

Referring still to FIG. 6B, four bolt slots 126 traverse the transducer body from one major side 112 to the second and opposite major side 114 for receiving bolts to attach the transducer 104 to the bottom of the prosthesis socket 60. The right side and left side of the transducer body include an elongated slot 128 extending from the anterior to the posterior side. The distance between the slot on the right and left sides corresponds to the spacing between two prongs of the bracket 108 that are used for connecting the transducer 104 to the master unit 106.

On the major side 114 opposite to the side 112 containing the inverted pyramid 110, a cavity is provided in the body of the transducer 104 for the inclusion of various electronic components. A printed circuit board 130 holds the electronic components. The printed circuit board 130 includes circuits for signal conditioning, temperature compensation, analog-to-digital conversion, digital-to-analog conversion and a serial communication bus. Additionally, transducer calibration data are stored in an onboard memory. The memory may also serve to record data over an extended period of time, such as when a patient wears the prosthesis in the normal course of a day. Records of alignment analysis and other patient treatment data may also be stored in the onboard memory. Power to the transducer 104 and wireless telemetry of the transducer 104 output are provided for by the master unit 106. An input/output (I/O) connector 202 is provided at the posterior side of the printed circuit board 130 for receiving a communication plug 264 from the master unit 106. A simplified schematic diagram of the electrical components of the transducer 104 is provided in FIG. 9. Retaining cover 134 is provided adjacent to the printed circuit board 130. Retaining cover 134 is covered with an adhesive-backed insulating ID label 136. A hollow pin 138 traverses the centers of the printed circuit board 130 and the retaining cover 13, and is anchored in the transducer 104 body, thus anchoring these components and allowing clearance for socket liner locking pins. A dummy plug 140 can be inserted into the I/O connector 202 when not connected to the master unit 106 for preventing debris to enter and do damage to the components in the body of the transducer 104.

Figure 8:
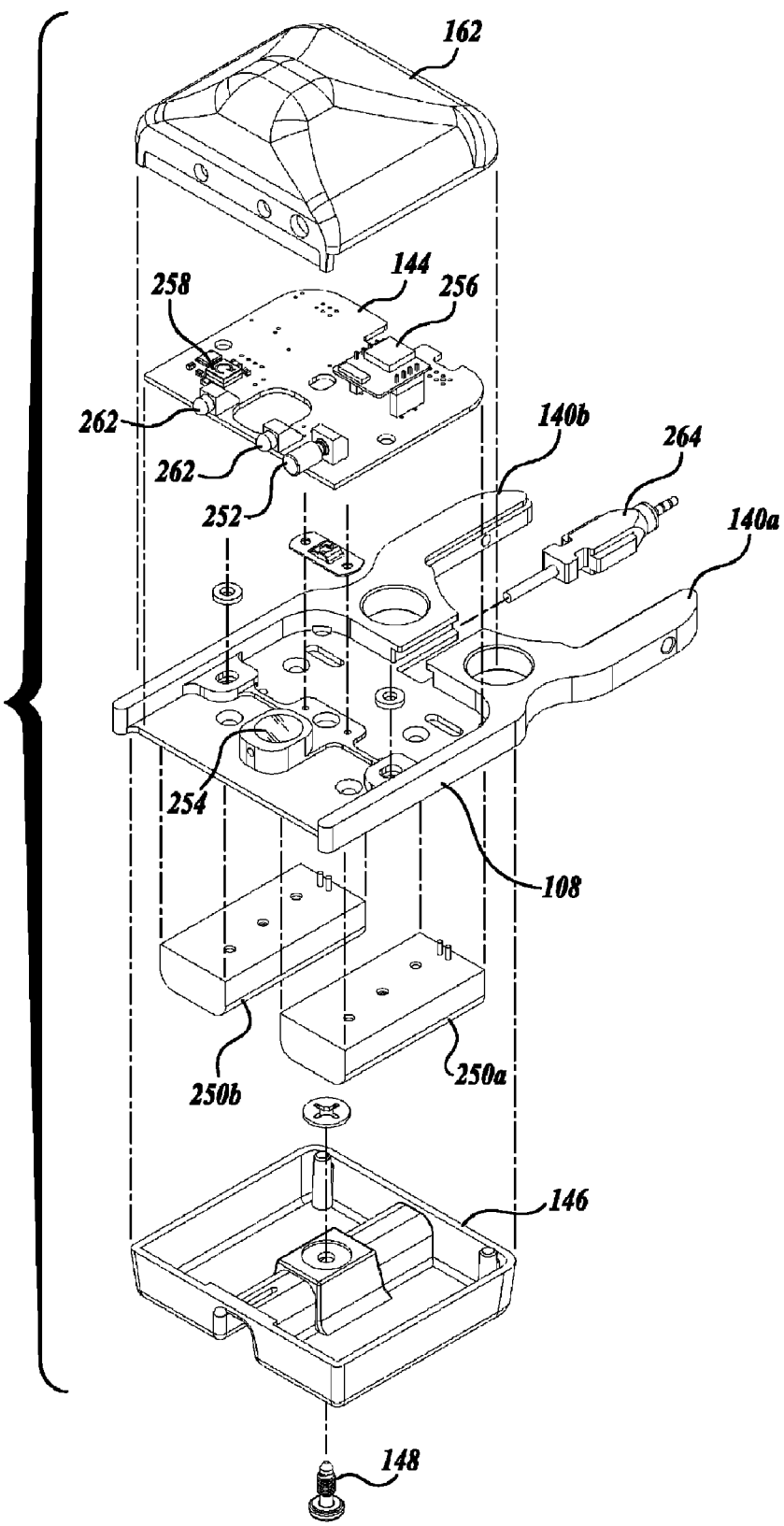
FIG. 8 is a diagrammatical illustration of an exploded view of a master unit in accordance with an embodiment of the present invention.

Referring to FIG. 8, the master unit 106 is illustrated. The master unit 106 includes the bracket 108 having a platform with details to provide for the support of the various components of the master unit 106. The bracket 108 has a first and second major side corresponding with the up and down direction. The bracket 108 includes a posterior platform that supports the master unit's 106 components. The bracket 108 includes a first and second prong 140a, 140b disposed on the anterior side. The spacing between the first and second prongs 140a, 140b matches the width of the transducer body at the slots 128 described above. On the underside of the bracket's 108 posterior platform, two rechargeable power units 250a, 250b, such as batteries, are provided. The batteries 250a, 250b are supported by a lower housing member 146 held to the bracket's 108 posterior platform via a screw 148. On the upper side of the bracket's 108 posterior platform, a printed circuit board 144 is provided for electrical components. A simplified schematic of the master unit's 106 components is provided in FIG. 10. The printed circuit 144 board supports a laser light line generator 254, status indicator lamps 262, a central processing unit 154, a gyroscope 258, and an input/output connector 264 that can be a plug, for example. The printed circuit board 144 is housed between the bracket's 108 posterior platform and the upper housing member 162.

Figure 9:
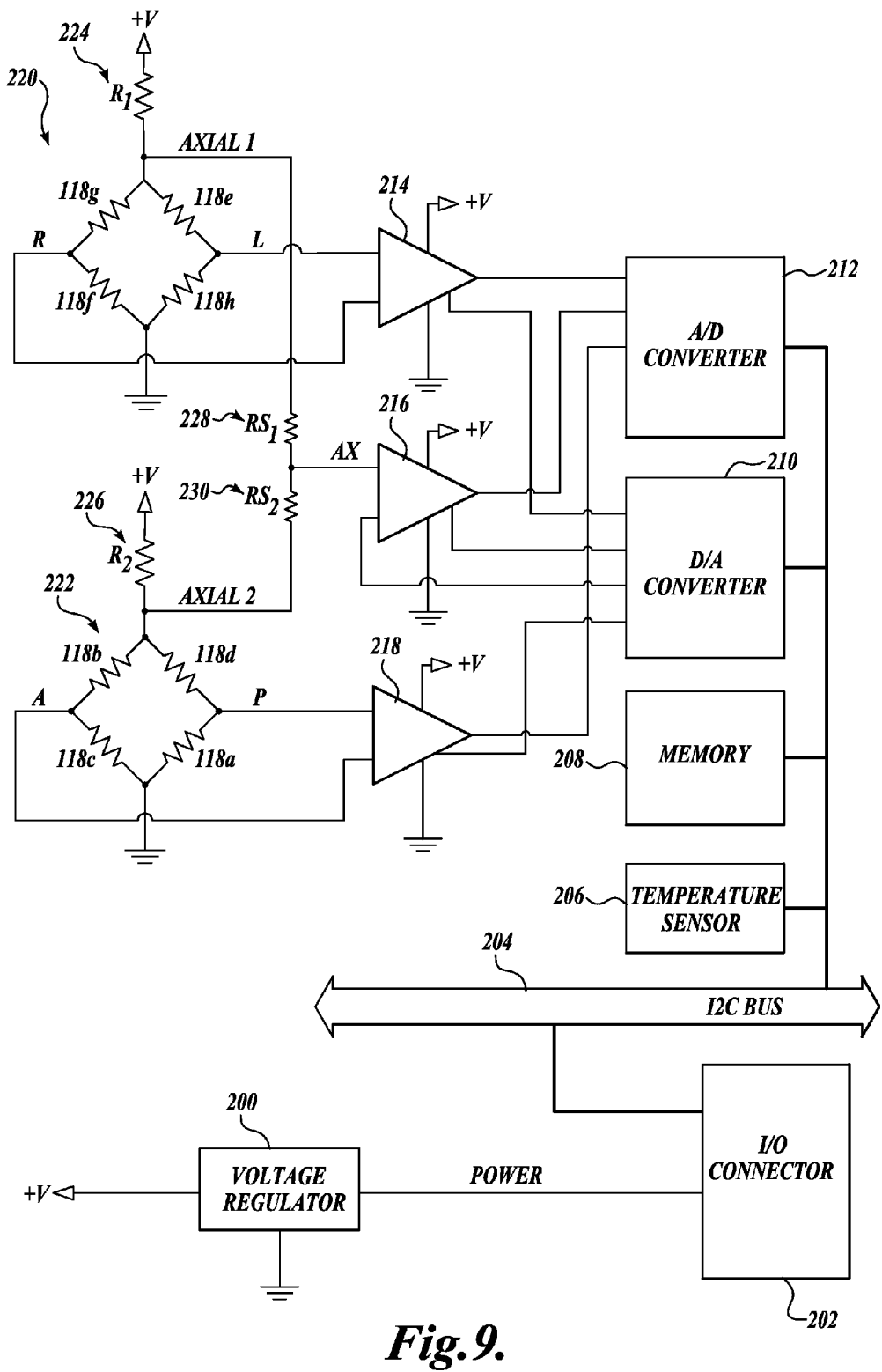
FIG. 9 is a simplified electrical schematic of the transducer of FIG. 6A.

Referring to FIG. 9, a schematic diagram showing the electrical components and configuration of the transducer 104 is provided. The transducer 104 includes an input/output connector 202 that can be a jack, for example. The input/output connector 202 receives voltage from a power source, such as the batteries 250a,b in the master unit 106. The voltage output from the master unit 106 is regulated by the voltage regulator 200 in the transducer 104. The input/output connector 202 is connected to power and a communication bus 204. The transducer 104 includes a temperature sensor 206. The temperature sensor 206 can be a thermistor that responds to changes in temperature by experiencing a change in resistance. The transducer 104 includes a memory 208. The memory 208 can be any volatile or non-volatile memory, such as, but not limited to, PROM, EEPROM, Flash, DRAM, eDRAM, and PROM to name a few representative examples. The memory 208 holds transducer calibration data and, alternatively, the memory 208 may hold data that is recorded over an extended period of time. Memory 208 may serve to record data over an extended period of time, such as when a patient wears the prosthesis in the normal course of a day. Records of alignment analysis and other patient treatment data may also be stored in the onboard memory 208. The transducer 104 includes digital-to-analog conversion circuit 210. The transducer 104 includes analog-to-digital conversion circuit 212. The transducer 104 includes various signal conditioning amplification circuits 214, 216, and 218. The temperature sensor 206, memory 208, digital-to-analog conversion circuit 210, and analog-to-digital conversion circuit 212 are connected to power and the communication bus 204. The eight strain gages 118a-118h are arranged into balanced bridge circuits 220 and 222. Each balanced bridge circuit 220 and 222 is connected to the voltage regulator 200.

Regulated voltage is applied through resistor 224 ($R_1$) to the balanced bridge circuit 220. Resistor 224 compensates for temperature effects on the strain gages 118e, 118h, 118f, and 118g to correct the differential output voltage for the right/left moment. The balanced bridge circuit 220 is connected to ground potential. The voltage differential output of the balanced bridge circuit 220 is amplified by the amplification circuit 214. The amplification circuit 214 is further connected to the voltage regulator 200. The amplification circuit 214 is further connected to ground potential. The output of the amplification circuit 214 is sent to the analog-to-digital conversion circuit 212.

Regulated voltage is applied through resistor 226 ($R_2$) to the balanced bridge circuit 222. Resistor 226 compensates for temperature effects on the strain gages 118d, 118a, 118c, 118b to correct the differential output voltage for the anterior/posterior moment. The balanced bridge circuit 222 is connected to ground potential. The voltage differential output from the balanced bridge circuit 222 is amplified by the amplification circuit 218. The amplification circuit 218 is similarly connected to the voltage regulator 200 and to ground potential. The output from the amplification circuit 218 is sent to the analog-to-digital conversion circuit 212.

The four strain gages 118e, 118h, 118f, and 118g are for measuring the right/left moments and are arranged into the first balanced bridge circuit 220. The voltage regulator 200 supplies power to the balanced bridge 220 via the resistor 224 ($R_1$) at a point between strain gages 118e and 118g. The ground or lower potential is at a point between strain gage 118h and strain gage 118f. A strain in the right/left plane results in a voltage difference measured between a point (R) located between strain gage 118g and strain gage 118f and a point (L) located between strain gage 118e and strain gage 118h. The voltage difference (R−L) output from the balanced bridge 220 is linearly related to the strain applied in the right/left plane and direction. For example, a push on the left side of the foot 20 stretches gages 118e and 118f and compresses gages 118h and 118g. The moment in the right/left plane is directly proportional to the voltage at R minus the voltage at L (the "RL" voltage), which is a positive number (and generates positive A/D counts). Gages 118c and 118b in the other bridge 222 may also be minimally stretched while gages 118d and 118a may be minimally compressed. This results in a nominal zero anterior/posterior output. A similar, but opposite effect is produced if the push is on the right side of the foot 20. The output voltage from the balanced bridge circuit 220 is amplified by an amplification circuit 214.

The four strain gages 118d, 118a, 118c, and 118b are for measuring the anterior/posterior moments and are arranged into the second balanced bridge circuit 222. The voltage regulator 200 supplies power to the balanced bridge circuit 222 via the resistor 226 ($R_2$) at a point between strain gages 118d and 118b. The ground or lower potential is at a point between strain gage 118a and strain gage 118c. A strain in the anterior/posterior plane results in a voltage difference measured between a point (A) located between strain gage 118b and strain gage 118c and a point (P) located between strain gage 118d and strain gage 118a. The voltage difference (A–P) output from the balanced bridge circuit 222 is linearly related to the strain applied in the anterior/posterior plane and direction. For example, a push on the heel of the foot stretches gages 118c and 118d and compresses gages 118a and 118b. The moment in the anterior/posterior plane is directly proportional to the voltage at A minus the voltage at P (the "AP" voltage) which is a positive number (and generates positive A/D counts). Gages 118f and 118g in the other bridge 220 may also be minimally stretched while gages 118e and 118h may be minimally compressed. This results in a nominal zero right/left output. A similar, but opposite effect is produced if the push is on the toe side of the foot 20. The output voltage from the balanced bridge circuit 222 is amplified by an amplification circuit 218.

The anterior/posterior and right/left signals generated by the transducer 104 are proportional to bending moments orthogonal with respect to the geometry of the transducer 104. For the signals to be useful for alignment of the prosthesis however, it is preferable that the transducer 104 also be aligned with a patient's line of progression as he/she walks, such that, for example, a moment at the base of the prosthesis socket 60, purely in the direction of the patient's motion, will produce a corresponding transducer output indicating an anterior/posterior moment, and no right/left output, whereas, if the transducer 104 were rotated relative to the line of progression, an erroneous signal would be present in the right/left output, and the anterior/posterior output would be reduced correspondingly. The computerized prosthesis alignment system 100 provides for a correction factor that takes into account a yaw angle deviation from a true line of progression. This correction factor is implemented by a computer application as will be described below. The transducer's 104 mounting slots 128 generally permit a posterior orientation adjustment to prevent the master unit 106 from hitting the other leg when walking.

Additional connections are established to measure the axial load experienced by the combined strain gages 118a, 118b, 118c, 118d, 118e, 118f, 118g, and 118h. The voltage to the balanced bridge circuit 220 after the resistor 224 (the "Axial 1" voltage) is averaged with the voltage of the balanced bridge circuit 222 after the resistor 226 (the "Axial 2" voltage). The Axial 1 voltage and Axial 2 voltage result from the voltage division of the source voltage by fixed resistors 224 ($R_1$) and 226 ($R_2$) and the algebraic sums of the voltages of the strain gages 118e, 118h, 118f, 118g and 118d, 118a, 118c, and 118b, respectively. The Axial 1 voltage and the Axial 2 voltage are electrically independent of differential voltages RL and AP. The averaged axial voltage signal at AX (FIG. 9) is not temperature compensated; however, compensation is done in software by monitoring transducer temperature with the temperature sensor 206 and applying an appropriate gain coefficient stored in memory 208. Resistors 228 ($RS_1$) and 230 ($RS_2$) are significantly larger than the strain gage resistances so as to have negligible effects on the voltage measurement at the bridges 220 and 222. The averaged voltage AX is amplified by the amplification circuit 216. This voltage represents the net axial load on the strain gages 118a-118h. The amplification circuit 216 is connected to the voltage regulator 200 and to ground potential. The output from the amplification circuit 216 is sent to the analog-to-digital conversion circuit 212. This voltage is a measure of the net axial force on the transducer 104, from which the weight of the patient can be extracted. Increasing the axial compression load results in negative voltage change and negative A/D counts. The output, however, may not be linear. A correction is done in software based on calibration data stored in memory 208.

Each of the amplification circuits 214, 216, and 218 mentioned above is further connected to the digital-to-analog conversion circuit 210. The analog-to-digital conversion circuit 212, the digital-to-analog conversion circuit 210, the memory 208, and the temperature sensor 206 are further connected to the communications bus 204. The transducer 104 includes a data communications protocol. In one embodiment, the data communications protocol is the $I^2C$ serial communication protocol for communication between the transducer 104 and master unit 106.

A further response is experienced on the axis of the inverted pyramid 110 that is the result of moment in the plane horizontal to the ground, or the transverse moment. In response to moment in this direction, strain gages 118e, 118g, 118a, and 118c are stressed in one direction while gages 118h, 118f, 118d, and 118b are stressed equally but in the opposite direction. The strain gages have been arranged to substantially cancel the response from moment in the transverse plane. This results in nominally zero outputs in the AP and RL voltages.

Trimmer resistors or potentiometers may be used to cancel out minor variations between the multiplicity of strain gages and balance the bridge circuits 220 and 222. However, the use of such resistors or potentiometers can be avoided by compensating for the offset in the bridge circuits' 220 and 222 output by varying the offset input to the amplification circuits 214, 216, and 218, including centering the amplification circuits' 214, 216, and 218 output in the range of the analog-to-digital conversion circuit 212. This is accomplished by the digital-to-analog conversion circuit 210 at the time when the system is "zeroed" under software control by reading the output value of the amplification circuits 214, 216, and 218 and adjusting the offset input by a corresponding value so as to achieve zero output. This has the advantage that the number of components is reduced, space and labor are conserved, dynamic range is maximized, and runtime calibration of the transducer 104 is permitted without physical disassembly or physical adjustment and allows the transducer 104 to be a substantially permanently sealed assembly.

Figure 10:
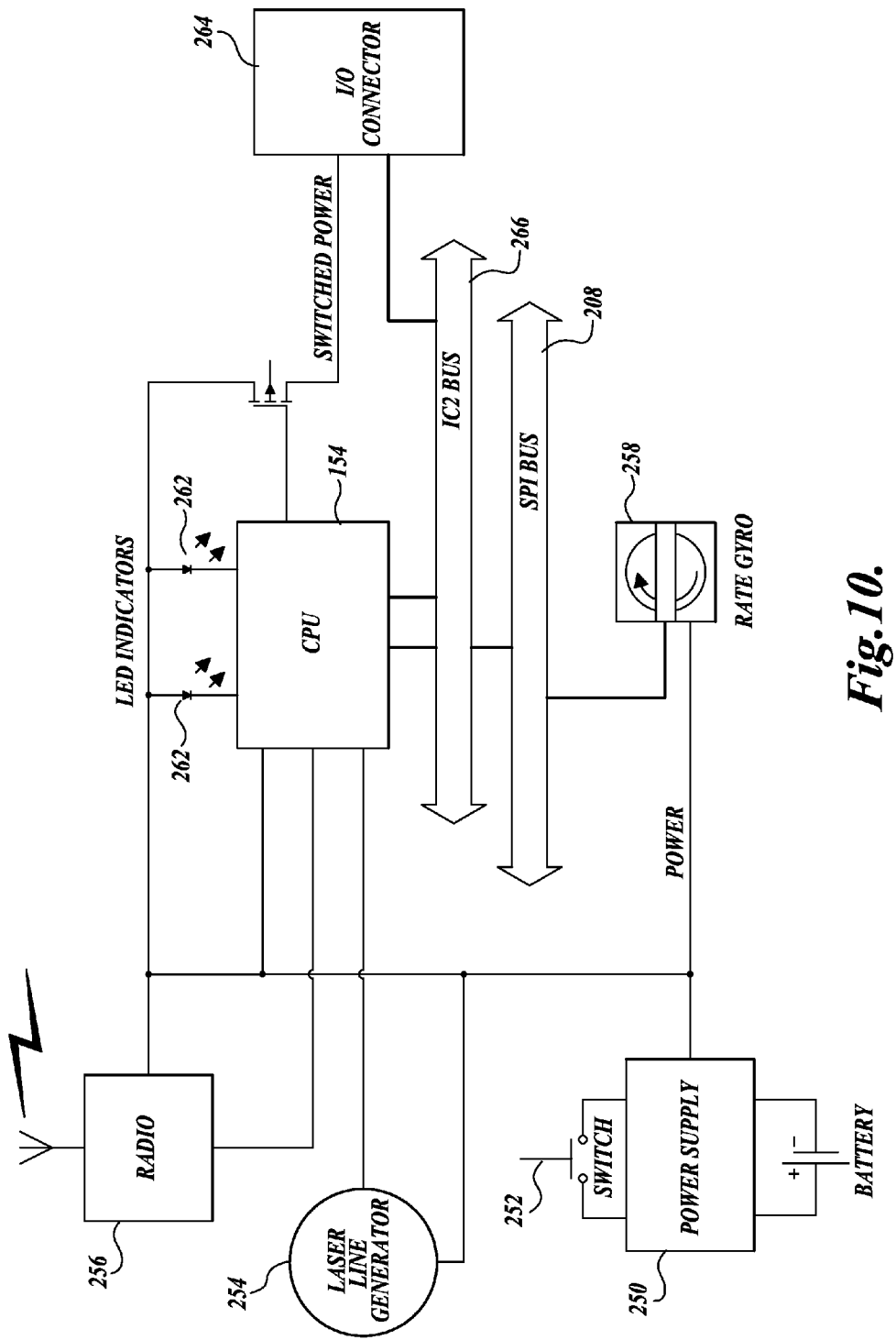
FIG. 10 is a simplified electrical schematic of the master unit of FIG. 8.

Referring to FIG. 10, the components of the master unit 106 are schematically illustrated. The master unit 106 includes a power supply 250, such as one or more batteries, coupled to a switch 252. The master unit 106 includes a laser light line generator 254 for generating a laser light that is aligned with a line of progression prior to the operation of the computerized prosthesis alignment system 100. The laser light line generator 254 is used in a method for aligning a prosthesis, described below. The master unit 106 includes a radio transmitter 256 and/or any type of wireless communication system for transmitting and receiving data wirelessly to and from a computer host. The wireless communications protocol may be any short-range radio frequency protocol, such as Bluetooth. The master unit 106 includes a rate gyroscope 254 used in calibrating the transducer 104 to a particular yaw angle setting. The yaw angle is the deviation from a reference in the horizontal plane. The rate gyroscope 254 is also used in the method for aligning a prosthesis. The master unit 106 further includes a central processing unit 154 for data processing and/or controlling the various other components. Additionally, the master unit 106 may include status indicators 262, such as light-emitting diodes. The master unit 106 supplies power to the transducer 104 via an input/output connector 264 and additionally receives input from the transducer 104 for processing via the central processing unit 154. The master unit 106 includes a communications bus 266, such as for the serial communications protocol I²C, and a serial-to-peripheral interface (SPI) bus 208. The various components described above may be communicatively connected to the central processing unit 154 in any manner to achieve the functionality that will be described below.

The applications running the computerized prosthesis alignment system 100 may be described in the context of computer-executable instructions, such as program modules being executed by the host computer. Generally described, program modules include routines, programs, applications, objects, components, data structures and the like, that perform tasks or implement particular abstract data types. The following description provides a general overview of a host computer system with which the method for aligning a prosthesis may be implemented. Then, the method for aligning the prosthesis will be described, including the use of applications on the host computer. The illustrative examples provided herein are not intended to be exhaustive or to limit the invention to the precise forms disclosed. Similarly, any steps described herein may be interchangeable with other steps, or a combination of steps, or be arranged in a different sequence in order to achieve the same result.

Figure 11:
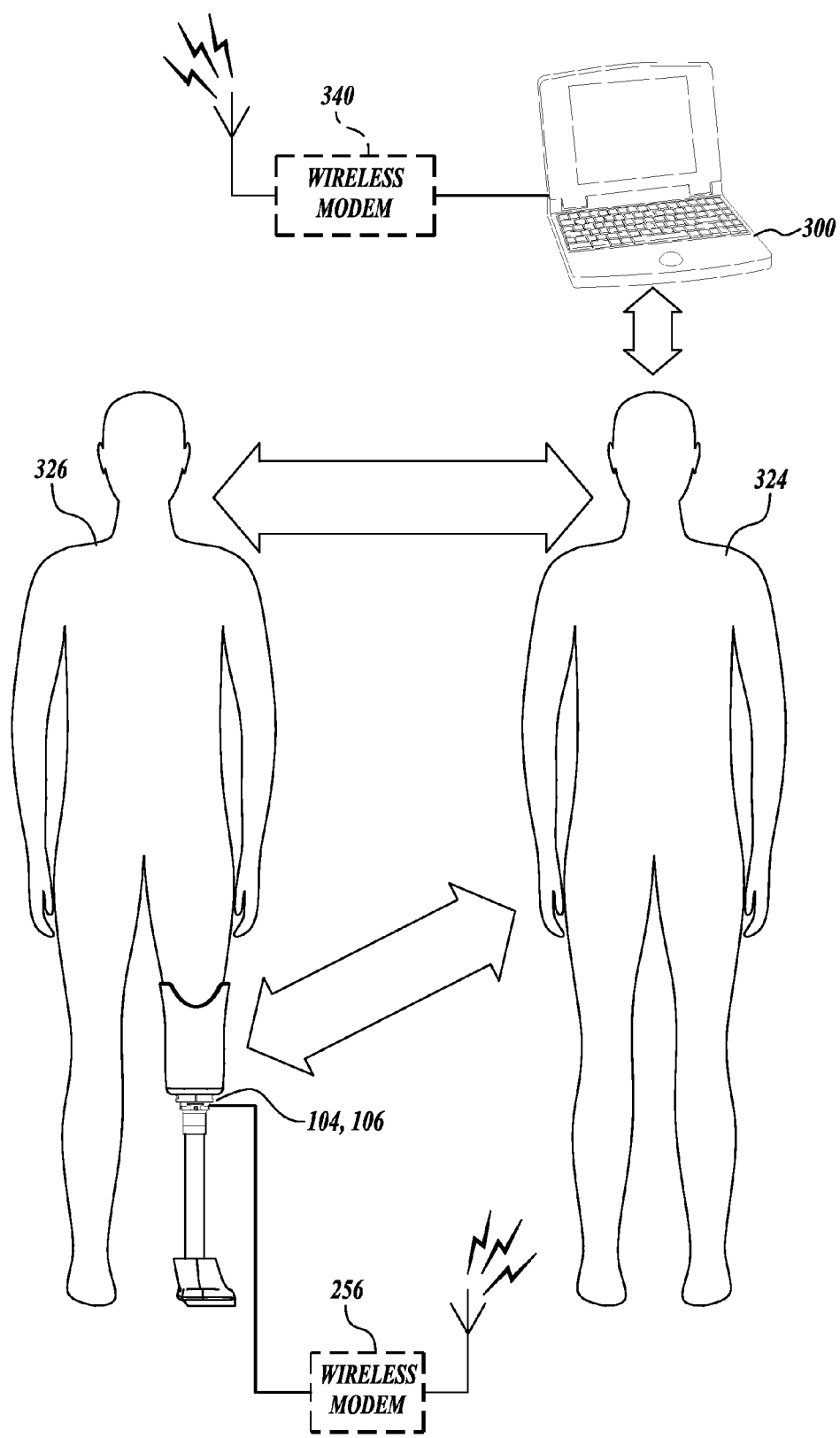
FIG. 11 is a diagrammatical illustration of an environment for the use of the computerized prosthesis alignment system of FIG. 4.

FIG. 11 illustrates an exemplary environment in which the computerized prosthesis alignment system 100 may be implemented. The computerized prosthesis alignment system 100 including the transducer 104 and master unit 106 are coupled to a prosthesis worn by a patient 326. The prosthetist or user 324 is available to directly communicate with the patient 326. The computerized prosthesis alignment system 100 uses a wireless modem 256 to communicate wirelessly to the host computer 300, which also includes a wireless modem 340. The user 324 may interact with the host computer 300 that runs applications, including a gait analysis application and a step and phase detection application. The host computer 300 uses a graphical user interface to communicate with the prosthetist 324.

Figure 12:
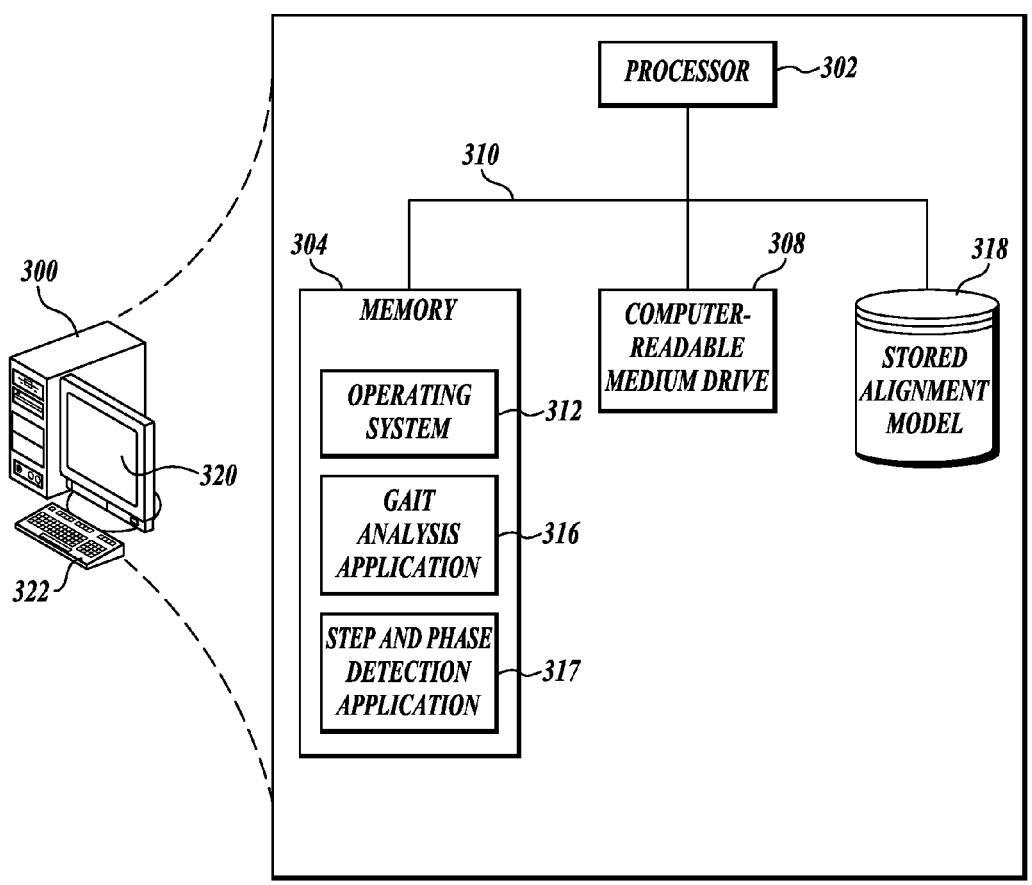
FIG. 12 is a diagrammatical illustration of a computer system for use with the computerized prosthesis alignment system of FIG. 4.

FIG. 12 illustrates an exemplary host computer 300 with components that are capable of implementing a method to align a prosthesis by conducting "gait analysis" using a gait analysis application 316 and a phase and step detection application 317 and providing feedback to the user 324 to achieve a suitable alignment. Those skilled in the art and others will recognize that the host computer 300 may be any one of a variety of devices including, but not limited to, personal computing devices, server-based computing devices, mini and mainframe computers, laptops, or other electronic devices having some type of memory. The host computer 300 depicted in FIG. 12 includes a processor 302, a memory 304, a computer-readable medium drive 308 (e.g., disk drive, a hard drive, CD-ROM/DVD-ROM, etc.), that are all communicatively connected to each other by a communication bus 310. The memory 304 generally comprises Random Access Memory ("RAM"), Read-Only Memory ("ROM"), flash memory, and the like. The host computer 300 also includes a display 320 and one or more user input devices 322, such as a mouse, keyboard, etc.

As illustrated in FIG. 12, the memory 304 stores an operating system 312 for controlling the general operation of the host computer 300. The operating system 312 may be a special purpose operating system designed for the computerized prosthesis alignment system 100. Alternatively, the operating system 312 may be a general purpose operating system, such as a Microsoft® operating system, a Linux operating system, or a UNIX® operating system. In any event, those skilled in the art and others will recognize that the operating system 312 controls the operation of the host computer 300 by, among other things, managing access to the hardware resources and input devices. For example, the operating system 312 performs functions that allow a program to receive data wirelessly over a radio receiver and/or read data from the computer-readable media drive 308. As described in further detail below, moment and axial load data in real time may be made available to the host computer 300 from the master unit 106 and from the computer-readable medium drive 308. In this regard, a program installed on the host computer 300 may interact with the operating system 312 to process the data received from one or both the master unit 106 and the computer-readable media drive 308.

As further depicted in FIG. 12, the memory 304 additionally stores program code that provides a gait analysis application 316 and a step detection application 317. The gait analysis application 316 includes computer-executable instructions that, when executed by the processor 302, applies an algorithm to receive, display, and process input, including moment and axial load data, to assist the user 324 in aligning a prosthesis. The gait analysis application 316, among other things, applies an algorithm to a set of moment data to correct for any horizontal rotational deviation of the transducer 104 during walking to the actual line of progression and then compares the corrected data to an optimal model of alignment stored on a device 318. The step and phase detection application 317 applies an algorithm to a set of moment and axial data to determine if the prosthesis is being used in steady state walking, and, if it is, the algorithm differentiates each step on the prosthesis and extracts the moment data beginning each step at initial contact and ending each step at the following initial contact in the gait cycle. Further, the step and phase detection application 317 establishes if the prosthesis is either in stance or swing phase of a gait cycle at each data point extracted for each step.

An overall method for aligning a prosthesis using the computerized prosthesis alignment system 100 begins with mounting the transducer 104 in the proper orientation to a prosthesis. The transducer 104 may be mounted directly at the base of the prosthesis socket 60. The inverted pyramid 110 may point up or down as needed to accommodate the setup of the individual prosthesis. The transducer 104 includes an anterior notch 118. The anterior notch 118 is oriented to point roughly in the anticipated anterior line of progression of the patient 326. The prosthesis is adjusted for the proper height of the patient 326 and the transducer 104 is initially roughly aligned. The master unit 106 may now be coupled to the transducer 104 via the prongs 140a and 140b at the anterior side of the bracket 108 to establish a rigid mechanical connection. The plug 264 of the master unit 106 is inserted to the I/O connector 202 of the transducer 104 to establish electrical and data communication connections.

Figure 13:
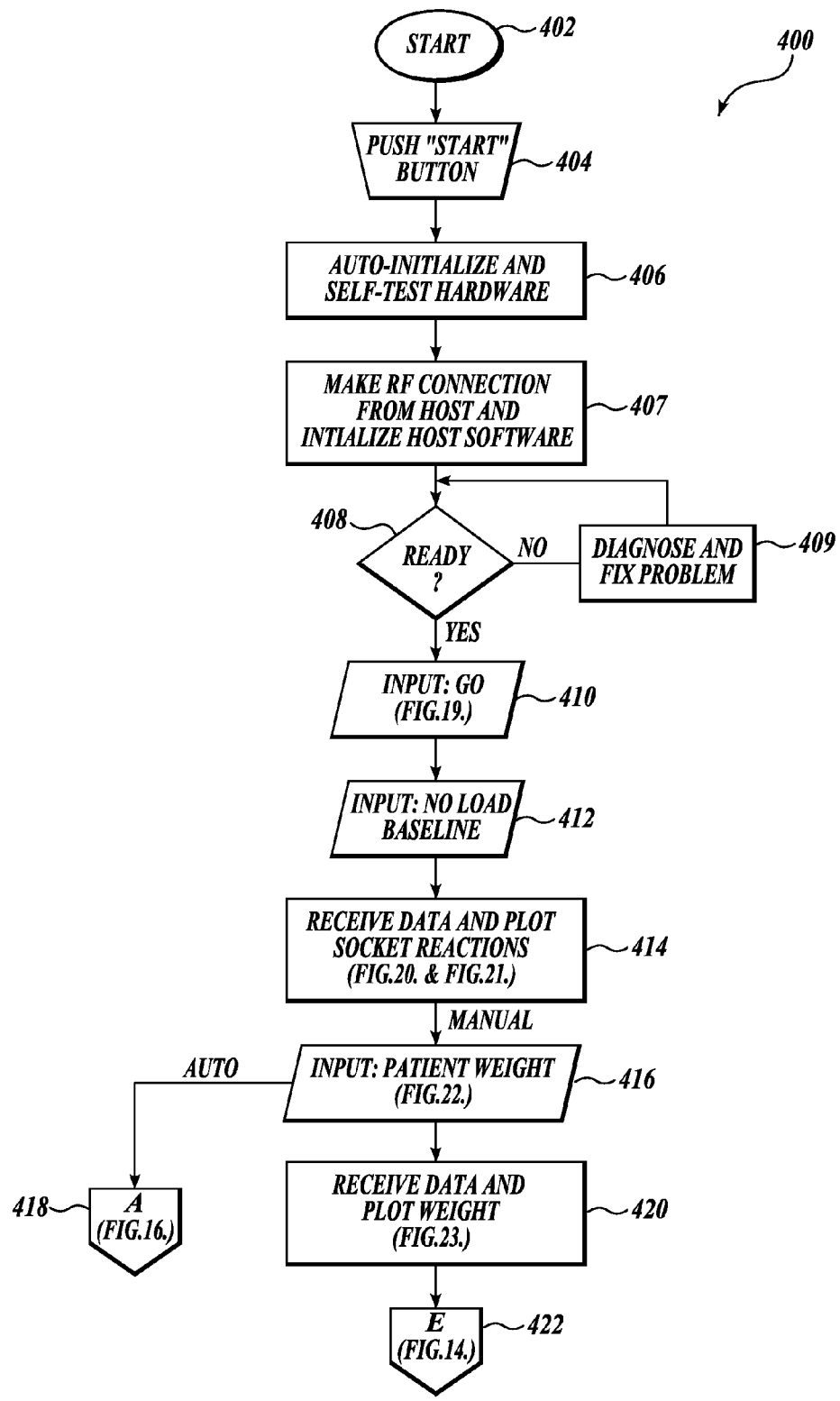
FIGS. 13-18 are flow diagrams of methods for a computerized prosthesis alignment system in accordance with one embodiment of the invention.

Referring to FIG. 13, a method 400 for aligning a prosthesis using the computerized prosthesis alignment system 100 is illustrated. The method 400 begins at start block 402. From start block 402, the method 400 enters block 404. In block 404, the user 324 is requested to push a start button on the master unit 106 that activates the computerized prosthesis alignment system 100. From start block 402, the method 400 enters block 406. In block 406, the computerized prosthesis alignment system 100 auto initializes itself and performs a self test on the hardware including the transducer 104 and the master unit 106. The automatic test of the system hardware will only take about one second. A steady amber "ready" light on the system indicates that the master unit 106 and transducer 104 is okay and ready to go. From block 406, the method 400 enters block 407. In block 407, the computerized prosthesis alignment system 100 makes a radio frequency connection to the host computer 300 and the host computer's 300 software is initialized. The host computer 300 will automatically connect to the computerized prosthesis alignment system 100 and perform automatic calibration of the transducer 104. The status of the startup process may be monitored by observing indicators on a graphical user interface appearing on the host computer's display 320. In one embodiment, the master unit 106 may use BlueTooth wireless technology for automatic pairing between the master unit 106 and the host computer 300 or any other computer running the gait analysis application 316 and the step and phase detection application 317. The computerized prosthesis alignment system 100 is designed to signal if there is a problem. For example, an indication of low battery power may be provided. If there are no problems, a status indicator may turn green.

From block 407, the method 400 enters block 408. In block 408, a determination is made whether the hardware is ready to receive user's 324 input. If the determination in block 408 is no, the method 400 enters block 404. In block 404, the user 324 may diagnose and fix the problem with the hardware and/or software of the computerized prosthesis alignment system 100, and from block 409, the method 400 reenters block 408. If the determination in block 408 is yes, meaning that the computerized prosthesis alignment system 100 is ready, the method 400 enters block 410. In block 410, the computerized prosthesis alignment system 100 receives input, such as "go" from the user 324 of the system 100. The user 324 can then graphically push a "go" button on the graphical user interface displayed by the host computer 300. See, for example, FIG. 19, button 802, which has been activated and is now labeled a "stop" button. The host computer 300 will then start to receive live information from the master unit 106. The user 324 may interact with the host computer 300 via the graphical use interface, embodiments of which will be described below in association with FIGS. 19-32. From block 410, the method 400 enters block 412. In block 412, the computerized prosthesis alignment system 100 receives input from the user 324 for the no-load base line. The no-load base line refers to the readings of the strain gages 116a-h from the transducer 104 measured when the patient 326 is not applying any weight on the prosthesis. With the computerized prosthesis alignment system 100 running, the patient 326 can lift the prosthesis vertically so it is slightly off the floor. The user 324 can then zero the transducer 104 to establish the no-load base line for the transducer 104. The user 324 interacts with the graphical user interface to zero the transducer 104. In one embodiment of the computerized prosthesis alignment system 100, the system 100 may be in one of three modes: setup mode, static mode, and dynamic mode.

The actions corresponding to each respective mode will be described below. Any mode may be entered from any other mode. Modes may occur simultaneously or may be entered in series and in any order. The user 324 may request, via the graphical user interface, to manually enter any mode; or upon completion of an action, any mode may be entered automatically, for example, by receiving a signal from a sensor, or upon completion of a step. In general, setup mode refers to the entry of input from the user 324 via the graphical user interface put up on the host computer's 300 display 320 by the gait analysis application 316 or via any other input entry means. Static mode generally refers to real time monitoring of information produced from the transducer's 104 output while the patient 326 is standing. In the static mode, for example, the gait analysis application 316 provides static "balance" information by supplying live anterior/posterior and right/left socket reaction graphs. Live graphs show the past second of data. Deviation from the zero level (balanced) of each graph directly indicates balance over the prosthetic foot 20. A live weight bearing graph may also be provided and may be used as biofeedback to show the patient 326 how much of their weight is being supported by the prosthesis. Static mode may also include providing the opposite limb loading if the patient's 326 weight has been entered at some time in the setup mode. In dynamic mode, generally, the patient 326 will be asked to walk to measure, record, and process anterior/posterior and right/left moments and perform analysis for providing alignment information to the user 324.

Returning to FIG. 13, from block 412, the method 400 enters block 414. In block 414, the host computer 300 begins to receive data and the host computer 300 plots socket reactions (moments) on the computer host's display 320. See, for example, FIGS. 20 and 21.

From block 414, the method 400 enters block 416. In block 416, the gait analysis application 316 receives the patient weight input. The patient weight input may be obtained via an automatic algorithm or via a manual input from the user 324. See, for example, FIG. 22. If the patient weight input is obtained manually, i.e., the user 324 can, via a graphical user interface brought up by the gait analysis application 316, enter the weight of the patient 326 and, the method 400 enters block 420, wherein the host computer 300 begins receiving weight data from the transducer 104 and plotting the weight data. See, for example, FIG. 23. If the patient weight input is obtained automatically, the method 400 enters the automatic patient weight input subroutine 500 beginning in block 418.

Figure 15:
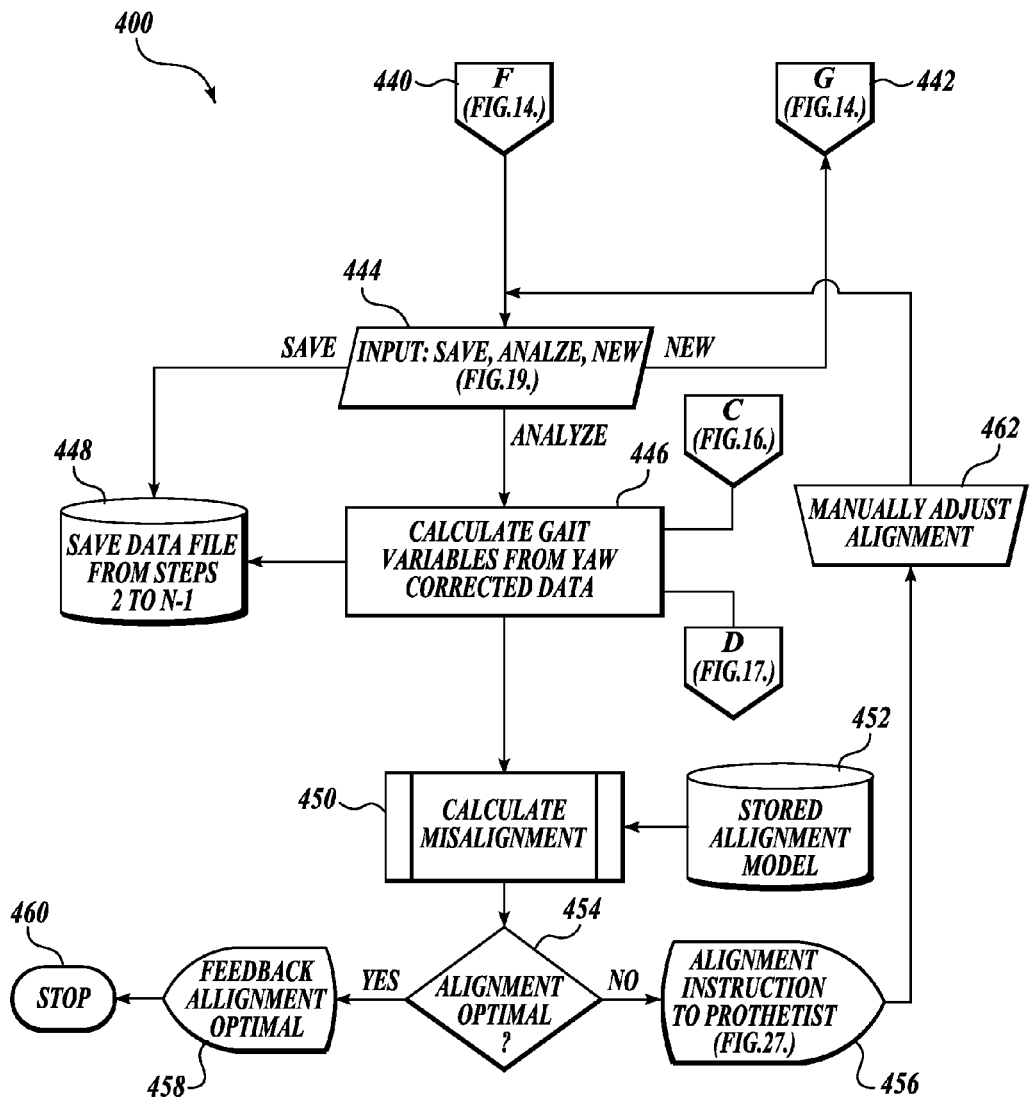
Figure 16:
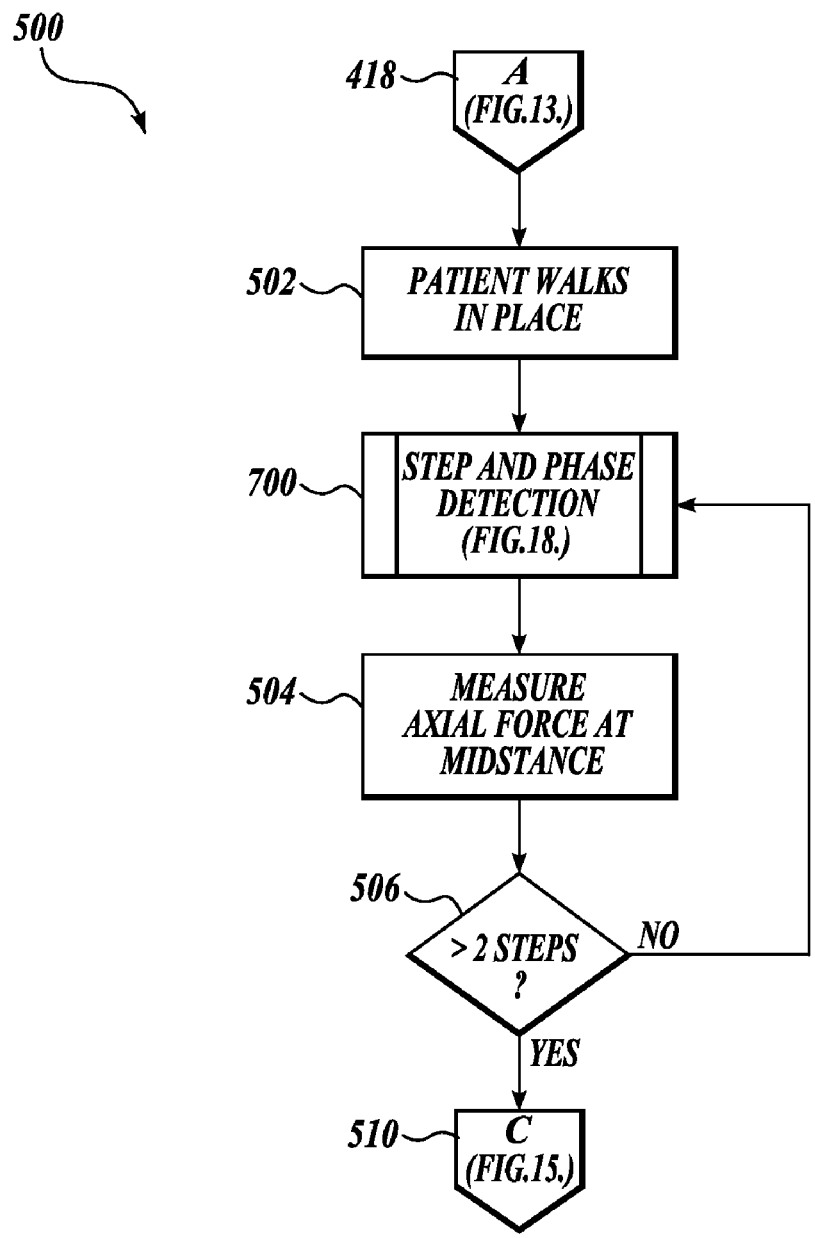

Referring to FIG. 16, the automatic patient weight input subroutine 500 begins at block 418. From block 418, the automatic patient weight input subroutine 500 enters block 502. In block 502, the patient 326 is asked to walk in place. From block 502, the automatic patient weight input subroutine 500 enters block 700. Block 700 is the step and phase detection application 317 that can determine the start, mid-stance, and end of a single step from the initial contact of the heel to toe off the ground. From the step and phase detection algorithm, the mid-stance is obtained to use in the automatic patient weight input subroutine 500. From block 700, the automatic patient weight input subroutine 500 enters block 504. In block 504, the automatic patient weight input subroutine 500 measures the axial force at the mid-stance of the step of the patient 326. From block 504, the automatic patient weight input subroutine 500 enters block 506. In block 506, a determination is made whether greater than two steps have been completed. The automatic patient weight input subroutine 500 can keep track of the number of steps by counting the number of initial contacts, toe-offs, or both. If the determination in block 506 is no, the automatic patient weight input subroutine 500 returns to block 700. If the determination in block 506 is yes, the automatic patient weight input subroutine 500 enters block 508. In block 508, the axial force at the mid-stance measured from more than two steps is calculated and used in the prosthesis alignment method 400 in blocks 416 or block 446 (FIG. 15).

Returning to FIG. 13, after the patient weight is input either through manual input or through automatic input, the method 400 enters a continuation block 422. Continuation block 422 indicates the method 400 is continued on FIG. 14.

Figure 14:
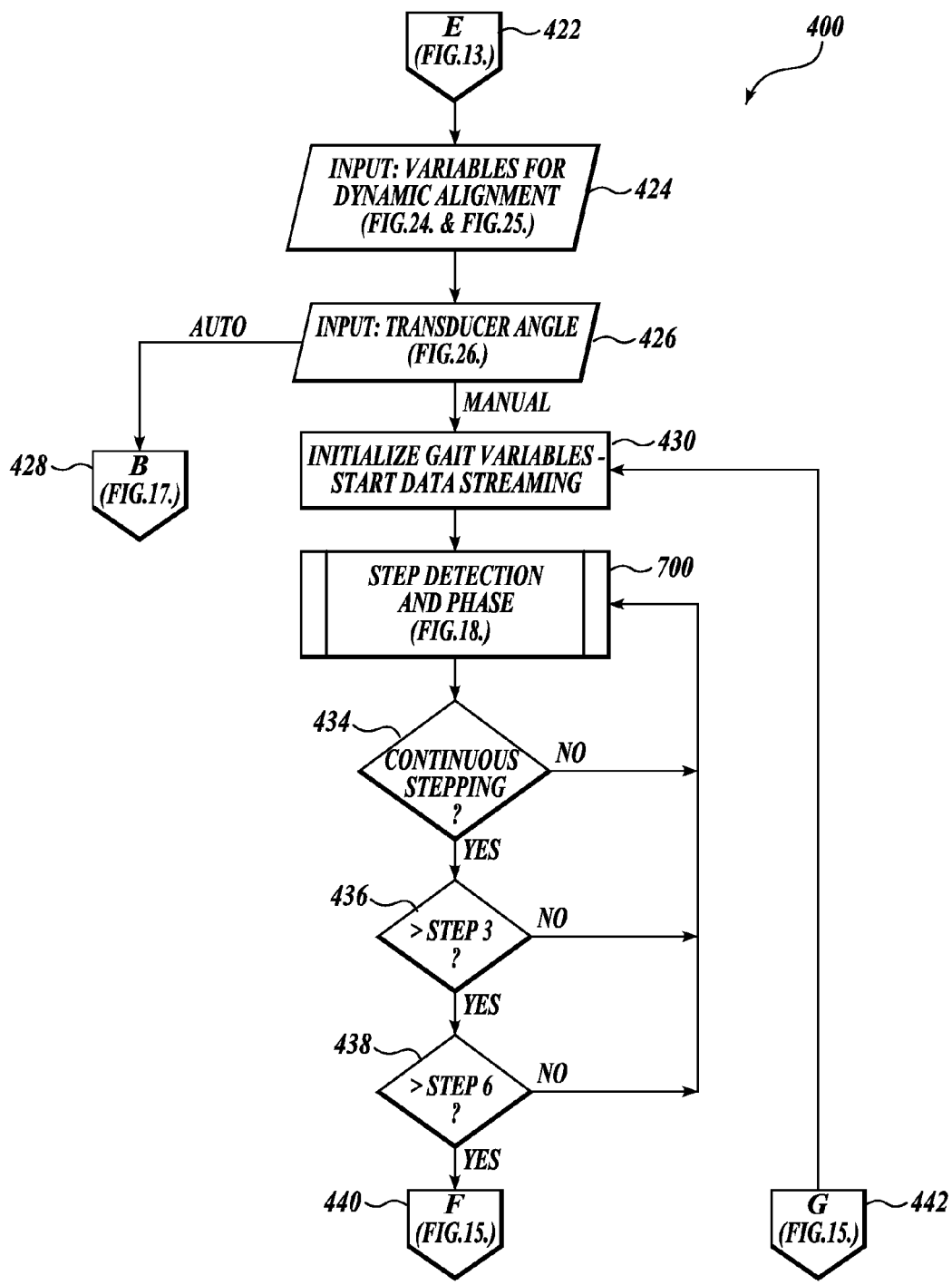

Referring to FIG. 14, continuation block 422 from FIG. 13 is followed by block 424. In block 424, variables for dynamic alignment are input. The variables may include the client identifier, the level of amputation, for example, transtibial or transfemoral, whether the left or right leg is being measured, whether the inverted pyramid 110 is oriented up or down, the transducer 104 height from the ground, the transducer 104 yaw angle with respect to a line of progression during walking, etc. The gait analysis application 316 may provide a graphical user interface for the purpose of entering variables. See, for example, FIGS. 24 and 25. For the transducer 104 height measurement, the measurement is taken from the "O" ring 122 at the base of the transducer 104 to the ground with shoe. The measurement is preferred to be to the nearest five millimeters or one quarter inch.

From block 424, the method 400 enters block 426. In block 426, the transducer angle is input. See, for example, FIG. 26. The transducer angle is a measure of yaw or horizontal deviation of the transducer 104 from a predetermined line of progression. The gait analysis application 316 analyzes the forces applied on the transducer 104 from the gait of the patient 326 in relation to the anatomical orientations of anterior/posterior and right/left sides of the patient 326. The transducer 104 angle setting allows the gait analysis application 316 to interpret the forces correctly, even if the transducer 104 is rotated several degrees from the true line of progression. The transducer angle may be input manually or via an automatic subroutine. The gait analysis application 316 brings up a graphical user interface for entering the transducer angle. Clicking on a transducer angle button will open a text box in which the user may directly enter an estimate of the rotation of the transducer 104 relative to a predetermined line of progression. If the transducer angle is input manually, the method 400 then enters block 430. For entering the transducer angle input automatically, the gait analysis application 316 provides a button on the graphical user interface to select automatic transducer angle input. The user 324 clicks on the button that launches a transducer angle input subroutine and the user 324 may follow the directions provided by the graphical user interface. The method 400 enters block 428. In block 428, the method 400 enters the transducer angle input subroutine illustrated in FIG. 17.

Figure 17:
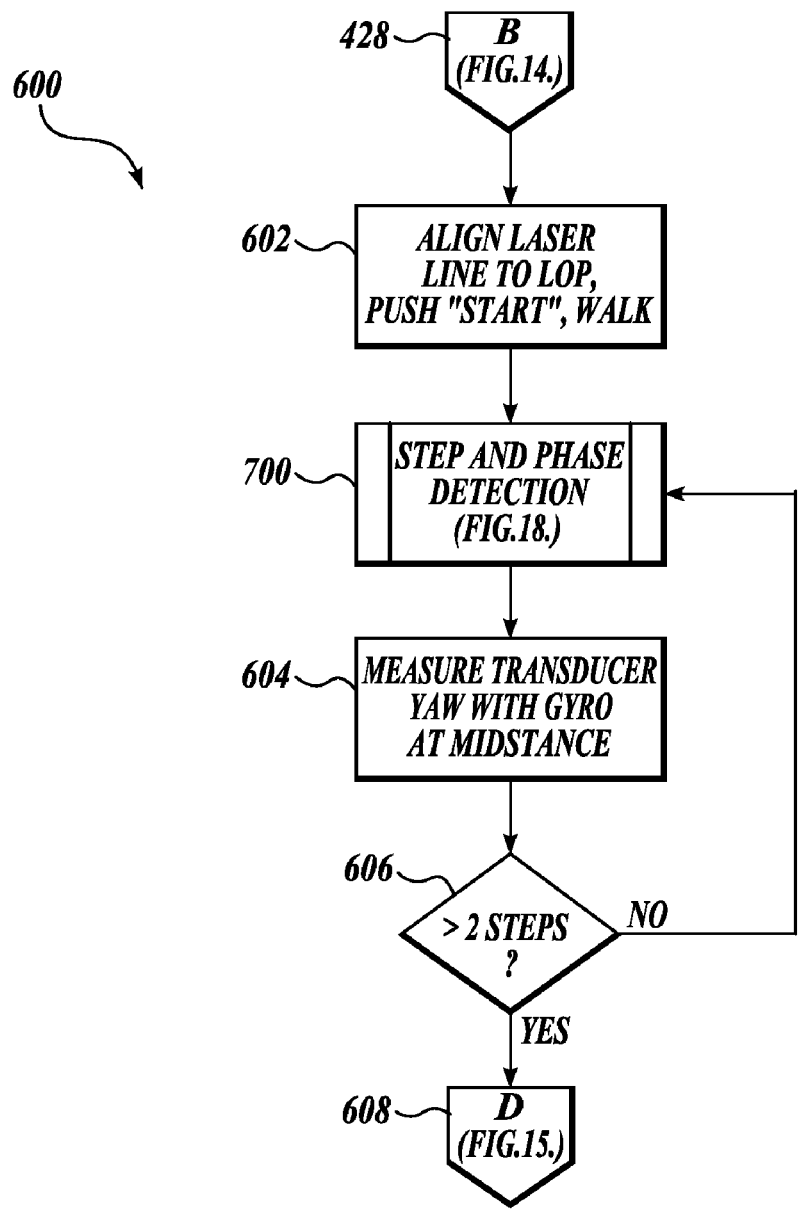

Referring to FIG. 17, from block 428 of FIG. 14, the transducer angle input subroutine 600 enters block 602. In block 602, the computerized prosthesis alignment system 100, and, in particular, the master unit 106 projects a laser line with the laser line generator 254 on the floor. Alternatively, the laser generator 254 may project a beam or spot. The laser line generator 254 may be factory aligned with the bracket 108 so that when attached to the transducer 104 and enabled by the gait analysis application 316, the laser line generator 254 projects the laser line onto the floor behind the patient 326 and parallel to the anterior/posterior plane of the transducer 104. The prosthesis with transducer 104 is rotated to align the laser with the predetermined line of progression of walking. With the transducer 104 so oriented, the rate gyroscope's 258 output is nulled on this heading. The line of progression may be any straight line on the ground or floor over which the patient 326 will be instructed to walk. Floor tile edges or a pattern in a carpet can provide a suitable line of progression. With the laser line projected on the intended line of progression, the user 234 pushes the start button on the master unit 106. The patient 326 is then instructed to walk along the line of progression and the gyroscope 258 output is sampled at mid-stance at one or more steps. The rate gyroscope 258 in the master unit 106 will track the rate of angle rotation with each step. This output signal from the rate gyroscope 258, when integrated over time represents the angle of the transducer 104 with respect to the line of progression which provides a correction factor needed to calculate the moments in the anterior/posterior and right/left planes. The correction may be done by physically rotating the transducer 104 as indicated by the calculated correction factor or by a mathematical correction applied to the transducer's 104 output signals.

From block 602, the transducer angle input subroutine 600 enters block 700. Block 700 is the step and phase detection application 317. From the step and phase detection application 317, the transducer angle input subroutine 600 utilizes input of the midstance of a step. From block 700, the transducer angle input subroutine 600 enters block 604. In block 604, the computerized prosthesis alignment system 100 determines the yaw from the rate gyroscope 258 at midstance to determine the deviation from the line of progression. This measurement is the transducer angle input. From block 604, the transducer angle input subroutine 600 enters block 606. In block 606, a determination is made whether greater than two steps have been completed. If the determination in block 606 is no, the transducer angle input subroutine 600 reenters block 700 to return to the step detection algorithm, and repeats until greater than two steps are completed. If the determination in block 606 is yes, the transducer angle input subroutine 600 enters block 608, wherein the laser line automatically turns off, indicating that the transducer angle measurement is complete and the transducer angle is input to block 426 (FIG. 14) and may also be used in block 446 (FIG. 15). The transducer angle input and/or any other setup information may be stored in the onboard memory 208 of the transducer 104 or in any other memory, such as memory 304 of the host computer 300.

From the transducer angle input subroutine 600, the method 400 returns to FIG. 14. From the sensor angle input block 426, the method 400 enters block 430. In block 430, the method 400 initializes the gait variables and starts data streaming to the host computer 300. At this point in the prosthesis alignment method 400, the gait analysis application 316 may bring up a graphical user interface providing the user 324 with selection buttons including: go/stop, new, analyze, and save. See, for example, FIG. 19. Generally, the user 324 is prepared to select the go button to allow streaming data from the computerized prosthesis alignment system 100 to the gait analysis application 316. While the data are streaming, the graphical user interface labels the button as a stop button. The graphical user interface may provide a data indicator to monitor the status, for example, an amber light if data collection is paused, and a green light if data is being streamed continuously.

Figure 18:
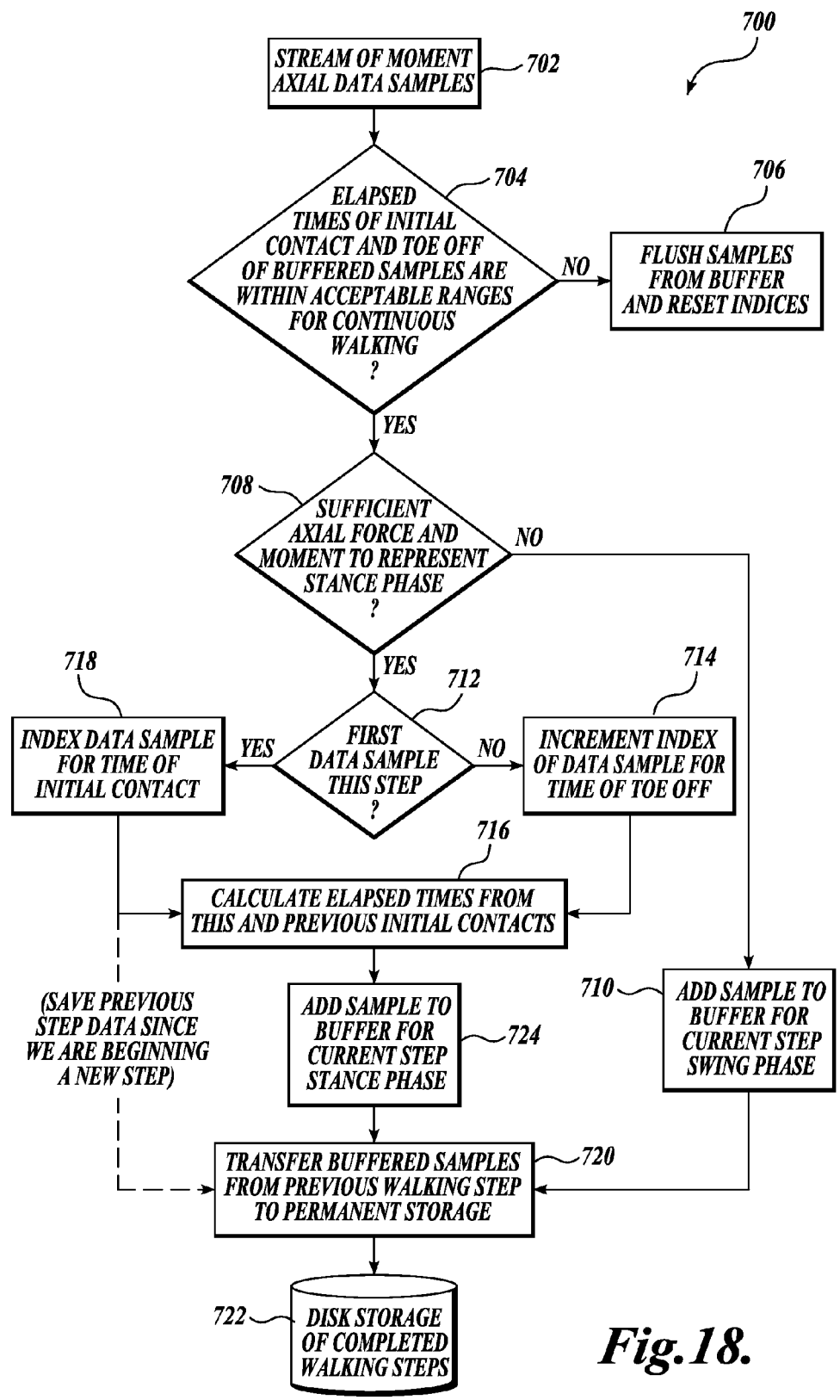

Data for analysis is preferably collected from a continuous stepping session during which the patient 326 does not pause or otherwise interrupt the flow of data for a minimum number of steps. Preferably too, the data for analysis is collected from a continuous stepping session so that any acceleration and deceleration effects are minimized when walking. A suitable continuous stepping session includes at least 3 steps in series, but need not be greater than 6 steps during any one continuous stepping session. Alternatively, at least 2 steps may be used. The step and phase detection algorithm 700 is employed to determine the start and stop of each step to count the number of steps during the session, and also to determine the mid-stance of each step for calculation of the axial load indicative of the weight bearing on the prosthesis. By using the readings of anterior/posterior moment, right/left moment, and axial force, the step and phase application 317 is able to identify the gait cycle, the stance and swing phase of each foot, and determine whether continuous stepping is occurring. This collection of data is described in FIG. 14 as blocks 700, 434, 436, and 438. From block 430, the method 400 enters block 700. Block 700 is the step and phase detection application once again that is illustrated in FIG. 18. From block 700, the method 400 enters block 434. Block 434 is for determining whether continuous stepping is occurring by receiving information from the step and phase detection application 317. If the determination in block 434 is no, the method 400 returns to block 700, the step and phase detection application 317. If the determination in block 434 is yes, the method 400 enters block 436. In block 436, the method 400 determines whether greater than three steps have been completed. If the determination in block 436 is no, the method 400 returns to block 700, the step and phase detection application 317. If the determination in block 436 is yes, the method 400 enters block 438. In block 438, the method 400 determines whether greater than six steps have been completed. If the determination in block 438 is no, the method 400 returns to block 700, the step and phase detection application 317. If the determination in block 438 is yes, the method 400 enters a continuation block 440. Continuation block 440 indicates that method 400 is continued in FIG. 15.

Referring to FIG. 15, from continuation block 440, the method 400 enters block 444. After collecting data, the gait analysis application 316 awaits the user's 324 input. Block 444 is for receiving input from the user 342. The gait analysis application 316 brings up a graphical user interface for providing options for the user 324. See, for example, FIG. 19. The graphical user interface may have "save," "analyze," and "new" buttons that the user 324 may select to save data, analyze data, or perform new data collection. If the user selects the new button, the gait analysis is based on a series of continuous steps that are selected by the gait analysis application 316 automatically. The user 324 may click on the new button to start collecting a new series of steps. Generally, the user 324 will click on the new button in the seconds before the patient 326 starts to walk. The new button is also selected whenever a change has been made to the alignment and the user 324 would like to measure with the realigned transducer 104. If the user 324 clicks on the save button, all, some, or none of the data can be saved to memory. At that point, the user 324 may start a new session by clicking on the new button so that the gait analysis application 316 then starts looking for a "new" series of steps to record once the patient 326 starts walking again. Once six steps have been recorded, the gait analysis application 316 will not add additional steps to the series. This limit of steps is variable, six being merely representative of one embodiment. The gait analysis application 316 may set a condition on whether to enable the analyze button. For example, the gait analysis application 316 may enable the analyze button when a minimum number of continuous steps are collected in series. A suitable number for analysis is four, but fewer or more steps may also be used.

In the method 400, from block 444, one of three blocks may be entered. From block 444, if the input to block 444 is "save," the method 400 enters block 448. In block 448, the method 400 saves into a data file, data collected from steps 2 to n−1. If the input in block 444 is "new," the method 400 returns via continuation block 442 to FIG. 14. Referring to FIG. 14, from continuation block 442, the method 400 returns to block 430 for initialization of the gait variables and starts data streaming once again. If the input in block 444 is "analyze," the method 400 enters block 446. In block 446, the method 400, calculates gait variables from the yaw-corrected data using input from the transducer angle calculation in FIG. 17, and the patient weight in FIG. 16. From block 446, the method 400 enters block 450. In block 450, the method 400 calculates the prosthesis misalignment. The gait analysis application 316 analyzes the patient's gait relative to an advanced mathematical model 318 of an ideal or optimal gait stored in the host computer device 300. The gait analysis application 316 determines the alignment change that would move the present alignment toward the model. For example, one embodiment for calculating the prosthesis misalignment may be to compare one or more of the gait variables collected during the walking session of the current patient 326 against the alignment model calculated from a larger database of gait variables collected from multiple and different patients from numerous prior sessions and stored in the device of the host computer 300. From block 450, the method 400 enters block 454. In block 454, the method 400 determines whether the present alignment is optimal by performing a comparison of the gait variables for the present session as compared with the stored alignment model 318. The alignment model block 452 supplies the alignment model to block 450 to determine misalignment.

To analyze for the misalignment, in one embodiment, the gait analysis application 316 calculates for each individual step, certain "gait" variables. Gait variables may include, but are not limited to, some or all of the anterior/posterior moment and right/left moment at each 20 percent increment in time of the stance phase from 0% to 100%; the maxima and minima of the anterior/posterior moment and right/left moment for the first and the last 50% of the stance phase; the slope of the change in anterior/posterior moment and right/left moment during each successive 20% time increment; and the integrated anterior/posterior moment and right/left moment measured over the period of each stance phase. The gait variables are then applied to a predefined model of alignment. The equations used in deriving the model of alignment are derived heuristically to minimize an external criterion called the Prediction Error Sum of Squares, or PESS, for previously measured socket reaction moments and axial force with a known set of geometric misalignments.

$$PESS = \frac{1}{N} \sum_{t=1}^{N} (y_t - f(x_t, \hat{a}_t))^2$$

Where N is the number of gait variable samples available, y is the target geometric misalignment, and â is an estimation of the combined parameters that describe the misalignment. The equation derivations are achieved using the Group Method of Data Handling described by Madala and Ivakhnenko (Madala, H., and Ivakhnenko, A., *Inductive Learning Algorithms for Complex Systems Modeling*, CRC Press, Boca Raton, Fla., USA, 1994). Solving the derived model equations with the gait variables calculated from the computerized prosthesis alignment system 100 data, results in a numeric estimation of the geometric misalignment in the prosthesis measured. For robustness, estimations from each of the equations becomes a vote added to a more generalized estimation of the misalignment.

Returning to FIG. 15, if the determination in block 454 is no, meaning that the alignment is not optimal, the method 400 enters block 456. In block 456, from the misalignment calculations described above, the gait analysis application 316 may provide verbal, textual, or graphic instructions to the user 324 as to which set screws 117 to loosen or tighten and to which side to move the transducer 104 to make the prosthesis alignment of the patient 326 similar to the optimal stored alignment model from block 452. Such corrective action can be provided to a user 324 via the host computer's 300 display 320 or, alternatively, the computerized prosthesis alignment system 100 may issue verbal instructions. See, for example, FIG. 27.

From block 456, the method 400 enters block 462. In block 462, the user 324 manually adjusts the alignment of the transducer 104 by adjusting the particular set screws 117 as instructed in block 456 and making the alignment of the transducer 104 in the anterior/posterior or right/left planes as provided by the instructions. From block 462, the method 400 enters block 444, where the user can save, analyze, or start a new data collection trial.

If the determination in block 454 is yes, meaning that the alignment is optimal, the method 400 enters block 458. In block 458, the method 400 indicates to the user 324 that the alignment of the prosthesis is optimal and no further corrections are necessary. From block 458 the method 400 enters block 460, where the method 400 stops.

When the user 324 has completed the dynamic alignment process using the computerized prosthesis alignment system 100, the user 324 can replace the transducer 104 with a substitute pyramid adaptor 105 seen in FIG. 5. The substitute pyramid adaptor 105 fits within the envelope of the transducer 104. The substitute pyramid adaptor 105 is the same height of the transducer 104, so that when the substitute pyramid adaptor 105 is substituted for the transducer 104, the alignment is retained. The transducer 104 may fit within the physical envelope of a conventional pyramid adaptor, so that the transducer 104 can be substituted with the substitute pyramid adaptor 105 having substantially similar dimensions as the transducer 104 so as not to alter the alignment achieved with the transducer 104. To swap the transducer 104 with the substitute pyramid adaptor 105, the user 324 marks the anterior notch 118 position on the prosthesis socket 60. The user 324 removes two adjacent alignment set screws 117 (for example, anterior and left) that hold the inverted pyramid 110 of the transducer 104. The transducer 104 may now be decoupled from the tube clamp adaptor 40. The four bolts in the slots 126 are removed to decouple the transducer 104 from the prosthesis socket 60. The substitute pyramid adaptor 105 is substituted for the transducer 104. The substitute pyramid adaptor 105 similarly includes an anterior notch. The anterior notch on the substitute pyramid adaptor 105 is matched with the mark made on the prosthesis socket 60. Thereafter, the four bolts attaching the pyramid adaptor 105 to the prosthesis socket 60 are replaced and the two adjacent set screws 117 that were previously removed are reinserted and tightened. The prosthesis now retains the same alignment that was achieved using the computerized prosthesis alignment system 100.

Alternatively, in another embodiment, the transducer 104 may remain incorporated in the prosthesis, and the patient 326 may use the prosthesis with the included transducer 104 in the normal course of walking for an extended period of time. During such extended period of time, the transducer 104 may continuously or semi-continuously record the socket reactions, i.e., the anterior/posterior, right/left moments, axial force, and any other data and store the information in the onboard memory 208. At a later time, the information from the onboard memory 208 may be retrieved and analyzed.

Before a description of the step and phase detection application 317, several terms need to be understood. A gait cycle is a repeat unit of the walking motion, for example, from initial contact of the heel of one foot to the subsequent initial contact of the heel of the same foot. The gait cycle of one foot includes a stance phase when the foot is in contact with the ground. The gait cycle includes a swing phase when the foot is not in contact with the ground. Initial contact is the start of the stance phase when the heel makes contact with the ground. Toe-off is the end of the stance phase when the toe leaves the ground. The swing phase occurs after toe-off and before initial contact of the heel. One swing phase and one stance phase complete a gait cycle.

Referring to FIG. 18, a flow diagram for the step and phase detection application 317 is illustrated. The step and phase detection application will be described in the context of a method 700. Generally described, the step and phase detection application 317 provides for real time analysis of the stream of moment and axial load data from the prosthesis alignment system 100 as discrete individual steps and by the phases (stance and swing) of gait of each step. The step and phase detection algorithm 700 provides for real time analysis of the stream of moments and axial load data from the prosthesis alignment system 100 as discrete individual steps taken during continuous walking and by the phases of gait of each step. The method 200 begins at block 702. In block 702, the method obtains a stream of moment and axial force data samples from the computerized prosthesis alignment system 100. From block 702, the method 700 enters block 704. In block 704, a determination is made whether the elapsed times of the initial contact and toe-off of steps are within acceptable ranges to define continuous walking. For example, each new data sample is evaluated first for the amount of time since the onset of both the last and the current weight bearing step. If the elapsed times are neither too long, indicating either standing or slow walking, or too short, indicating running, then the program enters block 708. If the elapsed time from the initial contact of the current step is too long or too short, then the data sample is considered to not be from steady state walking, and the method enters block 706 where the sample and any pending phase of gait indices are removed from memory. If the determination in block 704 is yes, the method 700 enters block 708. In block 708, the method 700 determines whether the prosthesis axial load is greater than a threshold which would occur without ambulation. If the determination is yes, then the data sample is considered to be within a stance phase of gait and the method 700 enters block 712. If the determination is no, the method 700 considers the data sample to be from the swing phase of gait and the method 700 enters block 710. In block 712, if the data sample is the first stance sample of the step, then the data sample is indexed as the initial contact time in block 718; otherwise, the sample is the last stance sample and is indexed as toe-off temporarily in block 714. Thereafter, each successive stance data sample will take the index of the toe-off sample in block 714 and calculate the elapsed time in block 714 and add the data sample to a buffer for the current step stance phase until the algorithm determines that the step is in swing phase once again. On the next occurrence of the first data sample being evaluated in stance phase (Initial Contact), the completion of the previous step is noted by transferring the stance and swing phase data buffers to an indexed array of complete individual steps and phase indices in block 720. This facilitates further analysis by the gait analysis application 316 by permanently storing the data on the computer readable medium in block 722.

For example, the step and phase detection application 317 may set a lower threshold of axial force below which, the stance phase is considered to not be occurring. If the determination in block 708 is no, the method 700 enters block 710. In block 710, the method 700 adds the data sample to a buffer and identifies it as a swing phase for the current step. If the determination in block 708 is yes, the method 700 enters block 712. In block 712, a determination is made whether the data sample is the first for the current step. Data samples can stream at several times per second so that for each step, the step is composed of several data samples. The data sample identifying the start of the stance phase is determined by the step and phase detection application 317. For example, by determining when the axial force is above a threshold. If the determination in block 712 is no, the method 700 enters block 714. In block 714, the method increments the index of a data sample for the time of toe-off. From block 714, the method 700 enters block 716.

If the determination in block 712 is yes, the method 700 enters block 718. In block 718, the data sample is indexed and identified with the time of initial contact.

From block 718, the method 700 may enter block 716 or block 720. Block 720 is entered when beginning a new step. The data from the previous step is saved. In block 720, the method 700 transfers buffered data samples from the previous walking step to permanent storage. From block 720, the method 700 enters block 722. In block 722, the method stores the data for the completed walking steps.

Otherwise, the method 700 enters block 716. In block 716, the method 700 calculates the elapsed time from the present and the previous initial contacts. From block 716, the method enters block 724. In block 724, the method 700 adds the data sample to a buffer for the current step and stance phase.

The gait analysis application 316 includes a graphical user interface for interacting with the user 324. Embodiments of the graphical user interface are illustrated in FIGS. 19-32.

Figure 19:
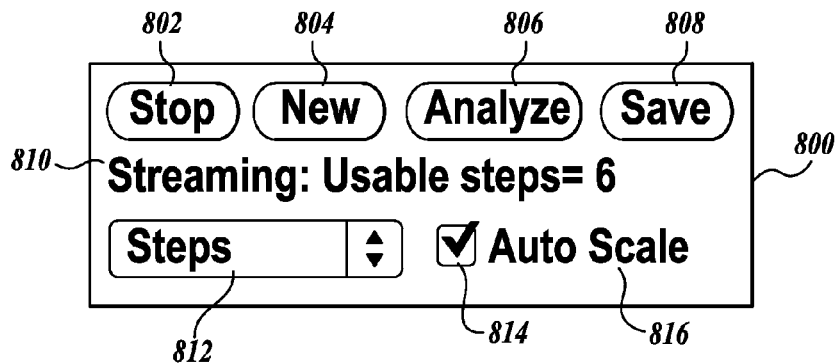
FIGS. 19-32 are illustrations of a graphical user interface in accordance with embodiments of the present invention.

FIG. 19 illustrates a graphical user interface 800 provided by the gait analysis application 316 for use in block 410 of method 400 in FIG. 13. The graphical user interface 800 provides to the user 324, the option to select from four buttons, including a go/stop button 802, a new button 804, an analyze button 806, and a save button 808. The graphical user interface 800 also includes a drop down menu 812 for selecting the number of steps to plot and a label 810 and text box showing the number of usable steps during streaming. The graphical user interface 800 also includes a check box 814 and label 816. The label 816 identifies the check box 814 is for auto scaling the plots of the moments. By clicking on the auto scale checkbox 814, the user 324 can automatically scale the graphs to a suitable range.

Figure 20:
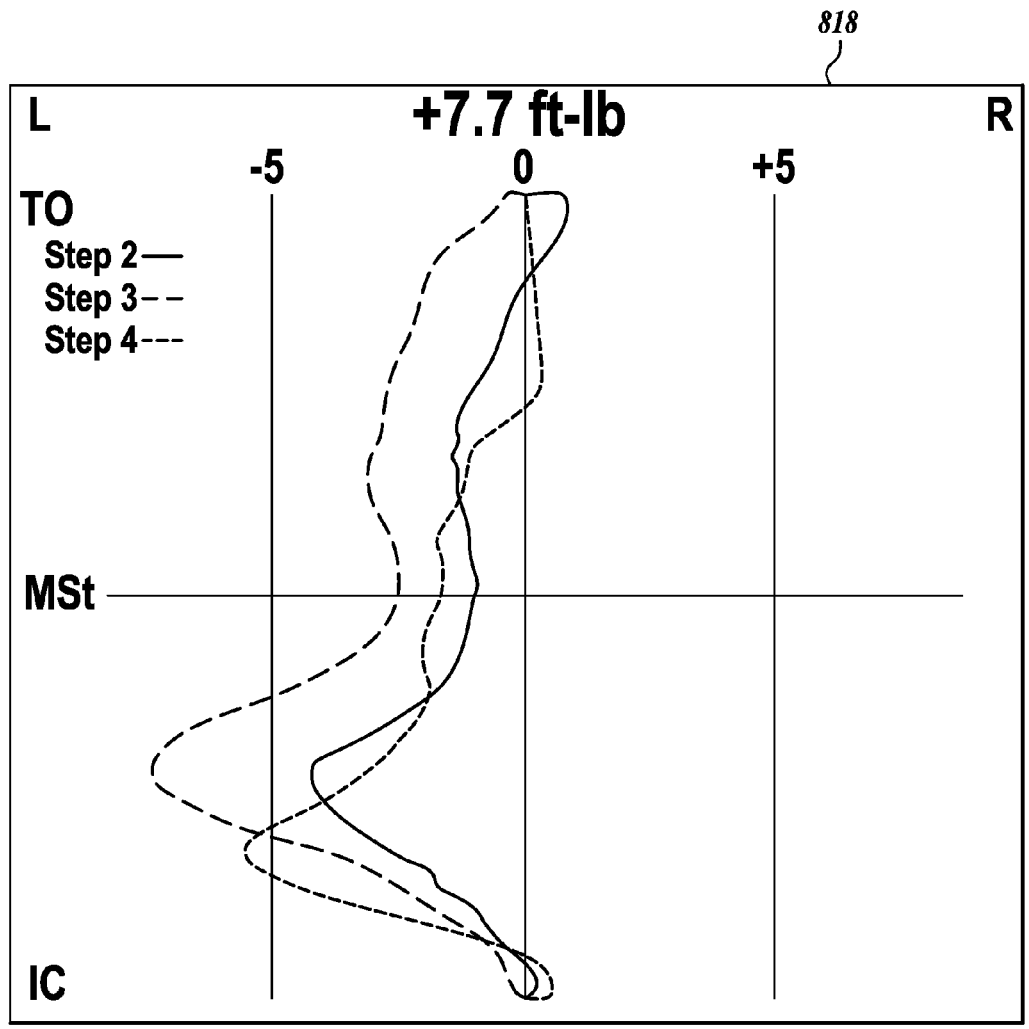

FIG. 20 is an illustration of a graph 818 of the right/left moment plotted for a stance phase from initial contact to toe-off for use in block 414 of method 400 in FIG. 13. A stance phase begins with initial contact (IC) of the heel with the ground and ends with toe off (TO) the ground. At the middle of the stance phase is the midstance (MSt). One or more stance phases can be plotted at a time on the graph. From the illustration, the graph indicates that the moment is generally negative. A rapid increase and decrease in negative moment from initial contact to midstance is noticed, followed by a gradual decline in moment.

Figure 21:
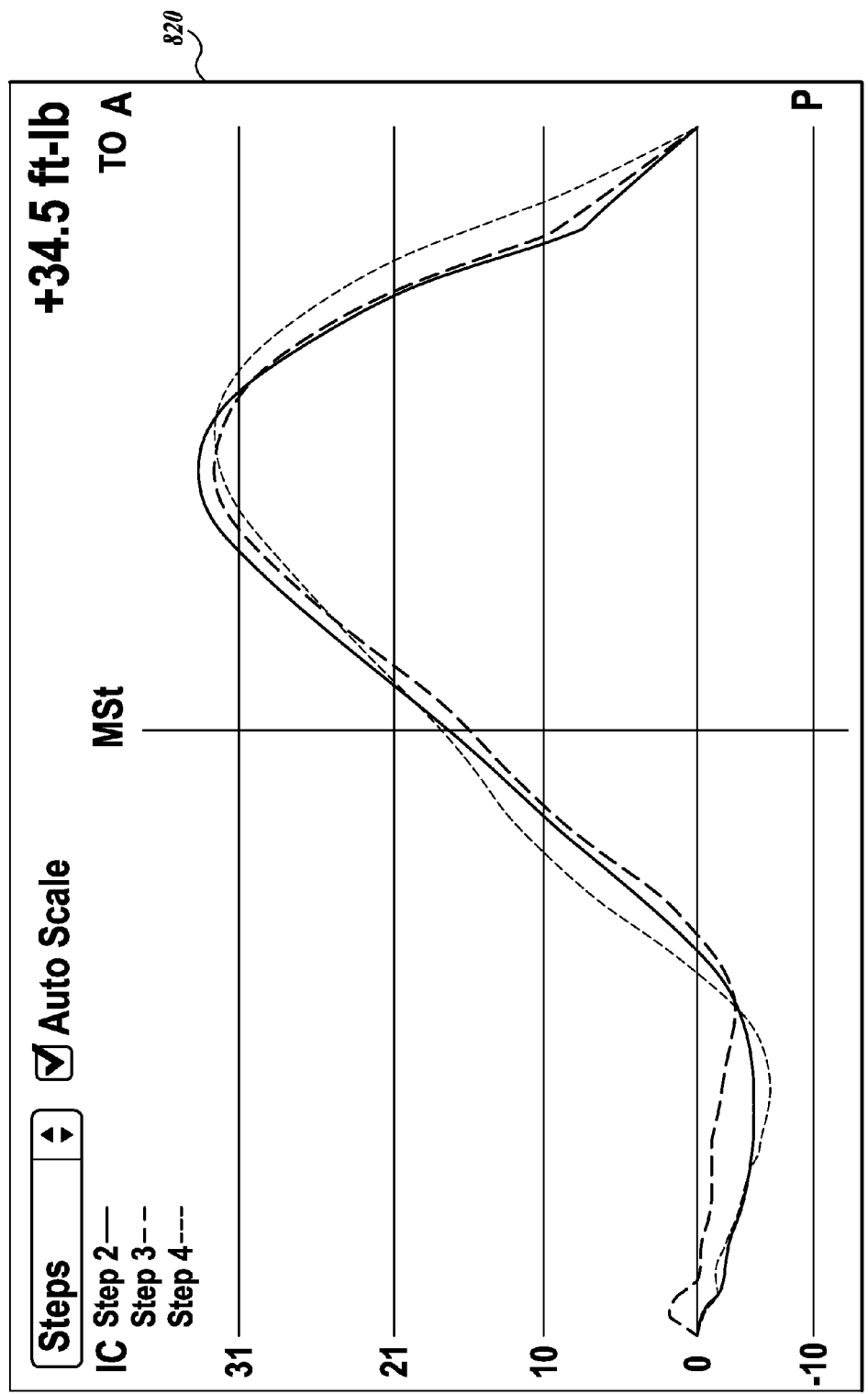

FIG. 21 is an illustration of a graph 820 of the anterior/posterior moment plotted for a stance phase for various steps for use in block 414 of method 400 in FIG. 13. From the illustration, there is an initial relatively small negative moment, followed by a rapid increase in moment at a point about half-way to the mid-stance and continuing past the mid-stance to reach a maximum at a point about half-way from mid-stance to toe-off, and followed by a rapid decline thereafter to toe-off.

Figure 22:
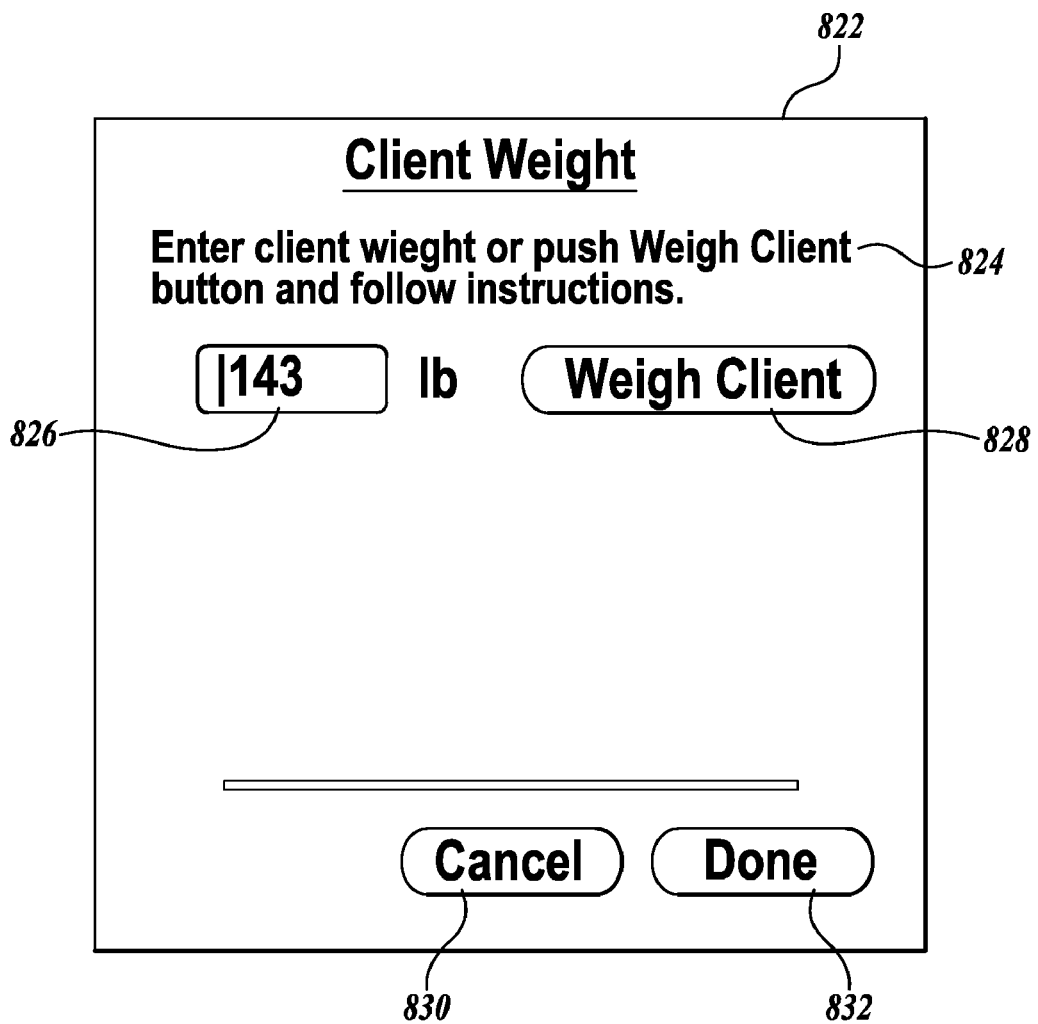

FIG. 22 is an illustration of a graphical user interface 822 for entering the patient 326 weight for block 416 of method 400 in FIG. 13. The graphical user interface 822 includes a text box 824 for providing instructions on entering the weight of the patient 326. The graphical user interface 822 includes a text box 826 for manually entering the weight of the patient 326. The graphical user interface 822 includes a weigh patient button 828 for automatically entering the weight of the patient 326. Clicking on the weigh patient button 828 calls up the automatic patient weight input subroutine 500 (FIG. 16). The graphical user interface 822 has a cancel button 830 and a done button 832. Clicking on the cancel button 830 closes the graphical user interface 822 without entering the patient 326 weight. Clicking on the done button 832 enters the patient 326 weight in the gait analysis application 316 and/or in the onboard memory 208 of the transducer 104 and may close the graphical user interface 822.

Figure 23:
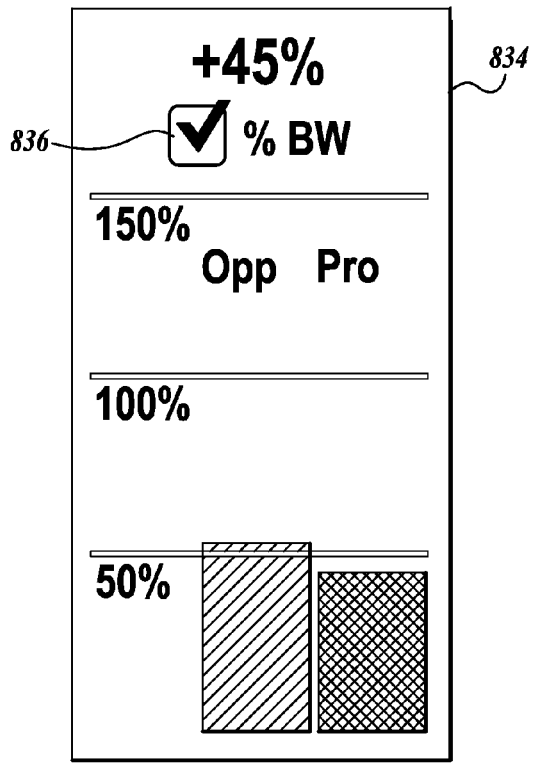

FIG. 23 is an illustration of a graphical user interface and bar graph 834 showing patient 326 weight information for block 420 of method 400 in FIG. 13. The bar graph 834 graphs the percent of the patient 326 weight supported by the prosthesis (PRO) and the opposite foot (OPP). The graphical user interface 834 includes a percent body weight (BW) checkbox 836. Clicking on the percent body weight checkbox 836 will show the information as a percentage of body weight. Specifically, FIG. 23 illustrates that the prosthesis bears slightly less than 50% of the body weight of the patient 326 during walking, and the opposite foot bears slightly greater than 50% of the body weight of the patient 236.

Figure 24:
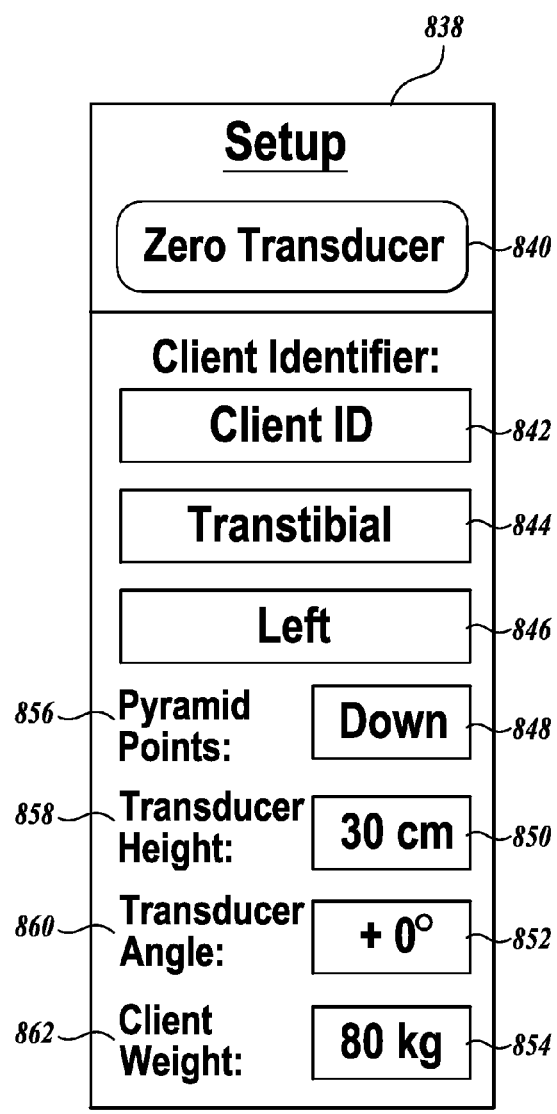

FIG. 24 is an illustration of a graphical user interface 838 for entering variables for dynamic alignment for block 424 of method 400 in FIG. 14. The graphical user interface 838 includes a button 840 for zeroing the transducer 104. The graphical user interface 838 includes a text box 842 for entering a client identifier. The graphical user interface 838 includes a text box 844 for entering the type of amputation, such as transtibial or transfemoral. The graphical user interface 838 includes a text box 846 for entering whether the prosthesis is for the left or the right leg. The graphical user interface 838 includes a label 856 and text box 848 for entering whether the inverted pyramid 110 is pointing in the down or up configuration. The graphical user interface 838 includes a label 858 and text box 850 for entering the height of the transducer 104. The graphical user interface 838 includes a label 860 and text box 852 for manually entering the transducer angle. The graphical user interface 838 includes a label 862 and text box 854 for manually entering the weight of the patient 326.

Figure 25:
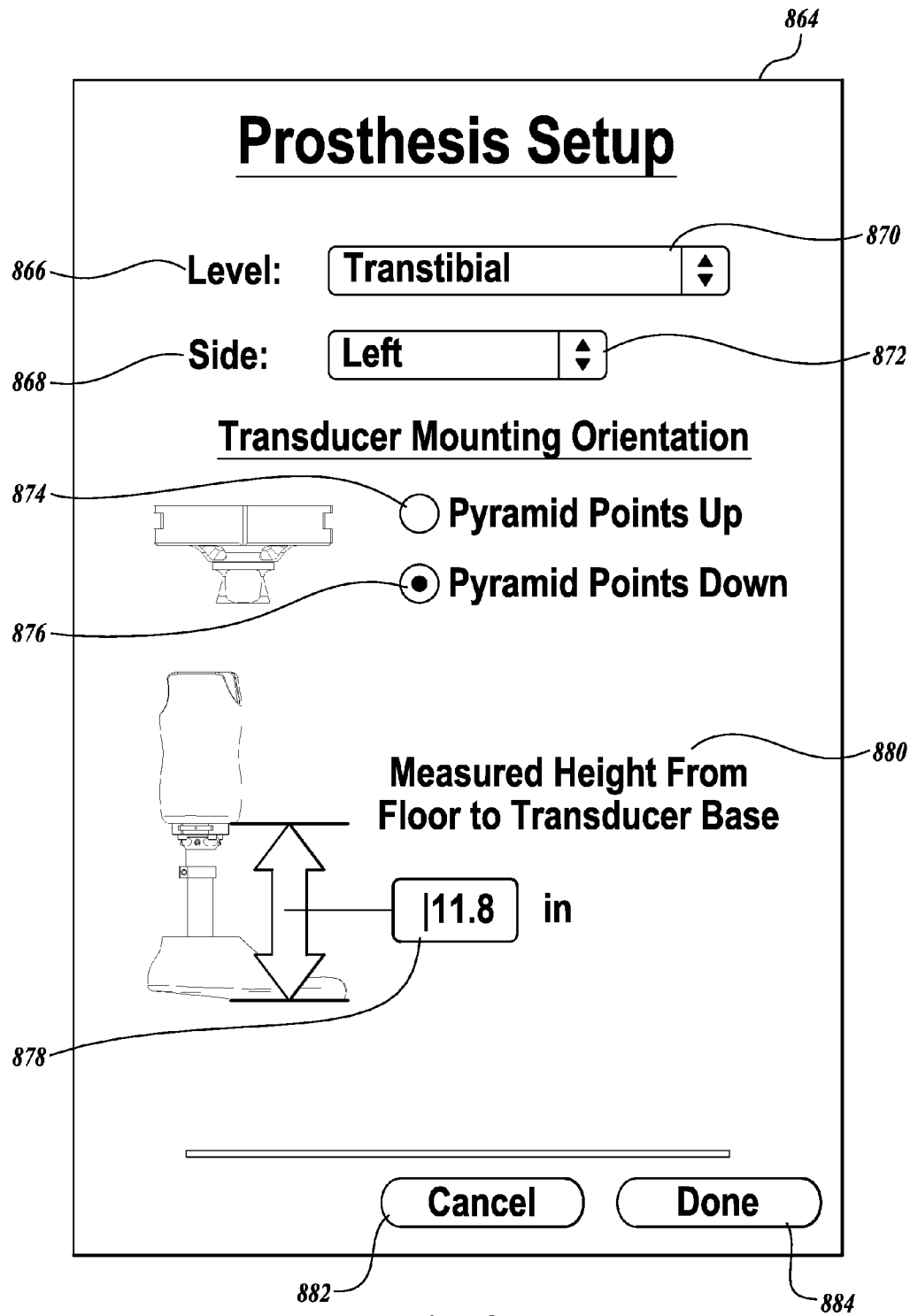

FIG. 25 is an illustration of another embodiment of a graphical user interface 864 for input entry for block 424 of method 400 in FIG. 14. The graphical user interface 864 includes a label 866 and dropdown menu 870 for selecting the level of the prosthesis, such as transtibial or transfemoral. The graphical user interface 864 includes a label 868 and dropdown menu 872 for selecting either the left or the right side corresponding to the amputation. The graphical user interface 864 includes radio buttons 874 and 876 for selecting whether the inverted pyramid 110 is configured in the up or the down direction. Selecting one radio button removes the selection of the other radio button. The graphical user interface 864 includes a label 880 and text box 878 for manually entering the height of the transducer 104 from the floor. The label 880 gives directions on measuring the height. The graphical user interface 864 includes a cancel button 882 and a done button 884. Clicking on the cancel button 882 closes the graphical user interface 822 without entering the setup information. Clicking on the done button 832 enters the setup information in the gait analysis application 316 and/or in the onboard memory 208 of the transducer 104 and may close the graphical user interface 864.

Figure 26:
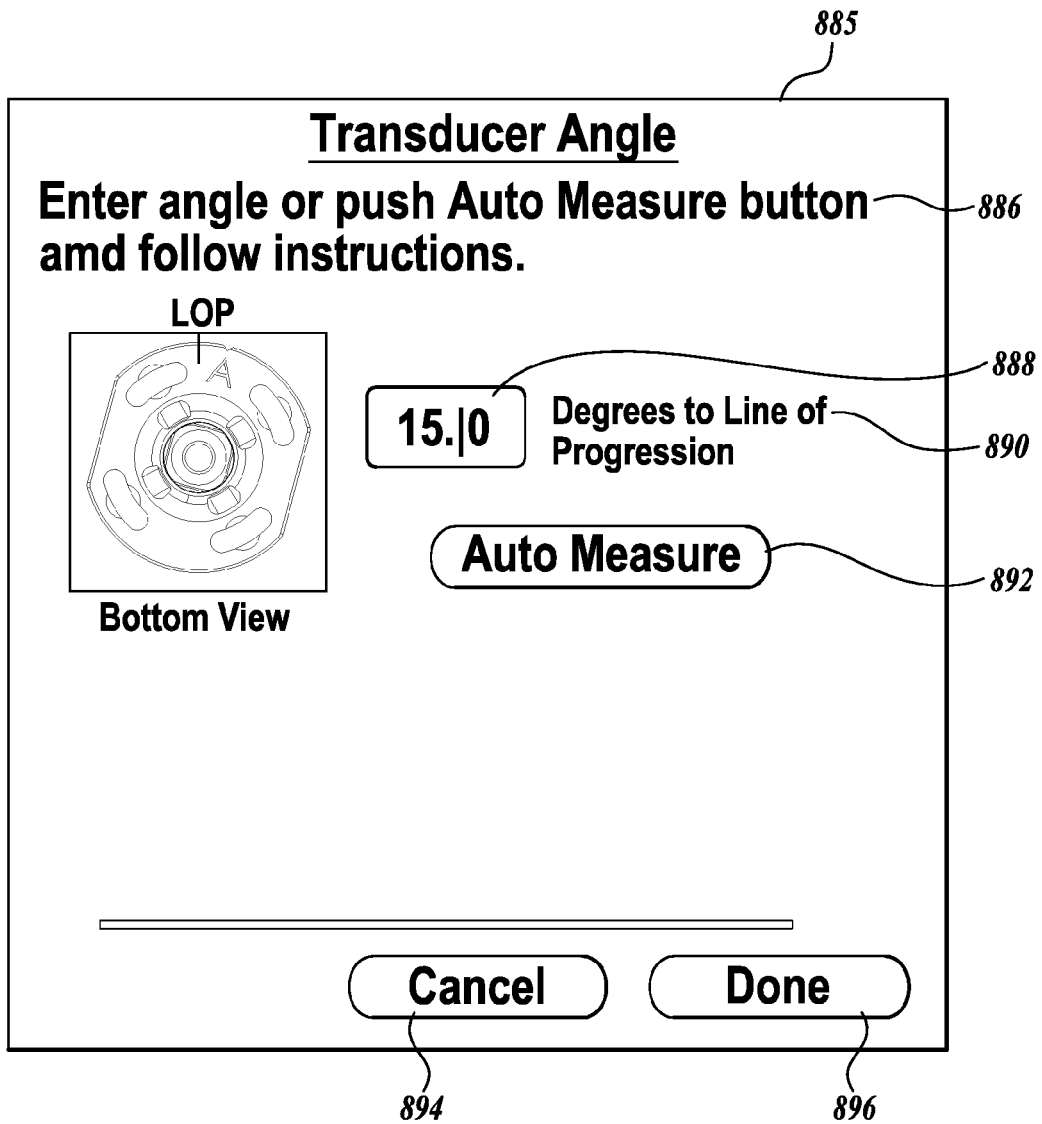

FIG. 26 is an illustration of a graphical user interface 885 for entering the transducer angle for block 426 of method 400 in FIG. 14. The graphical user interface 885 includes a label 886 for providing instructions to enter transducer angle manually or automatically. The graphical user interface 885 includes a label 890 and text box 888 for manually entering the degrees of yaw with respect to a predetermined line of progression. The graphical user interface 885 includes an auto measure button 892 for automatically measuring the yaw angle with respect to the predetermined line of progression. Clicking on the auto measure button 892 calls the transducer angle input subroutine of FIG. 17. The graphical user interface 885 includes a cancel button 894 and a done button 896. Clicking on the cancel button 894 closes the graphical user interface 885 without entering the transducer angle information. Clicking on the done button 896 enters the sensor angle information in the gait analysis application 316 and/or in the onboard memory 208 of the transducer 104 and may close the graphical user interface 885.

Figure 27:
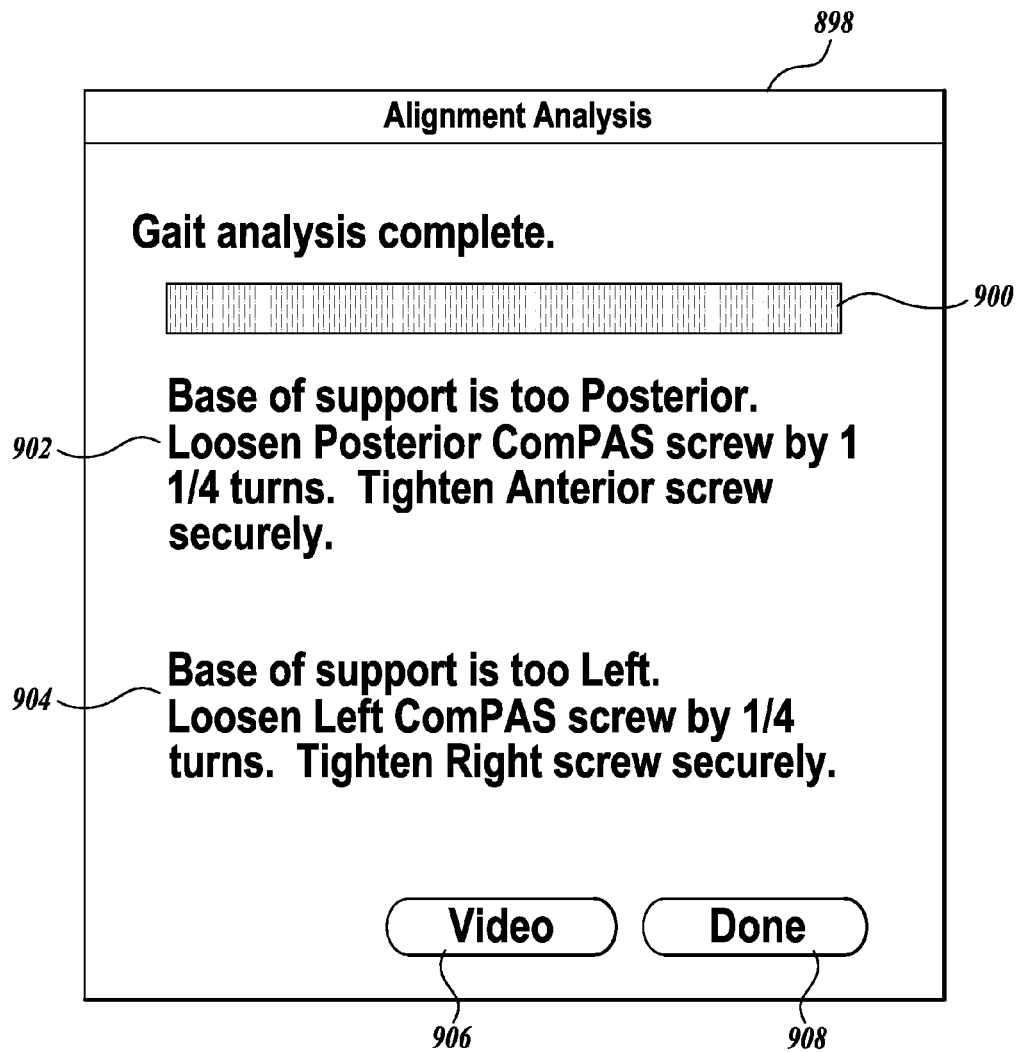

FIG. 27 is an illustration of a graphical user interface 898 for block 456 of the gait analysis application 316 of FIG. 12. The graphical user interface 898 includes a progress bar 900 for indicating the progress of the analysis. When the analysis is complete, the progress bar 900 is full. The graphical user interface 898 includes a first label 902 and a second label 904. The label 902 provides to the user 324, the alignment condition in the anterior/posterior plane and instructions for aligning the prosthesis in the anterior/posterior plane by identifying the set screw 117 or screws needing adjustment, and the amount of turns that are to be applied to the set screws 117. The label 904 provides to the user 324, the alignment condition in the right/left plane and instructions for aligning the prosthesis in the right/left plane by identifying the set screw 117 or screws needing adjustment, and the amount of turns that are to be applied to the set screws 117. The graphical user interface 898 includes a video button 906 and a done button 908. Clicking on the video button 906 brings up a video of a model patient 326 walking with the detected misalignment. Clicking on the done button 908 may close the graphical user interface 898.

Figure 28:
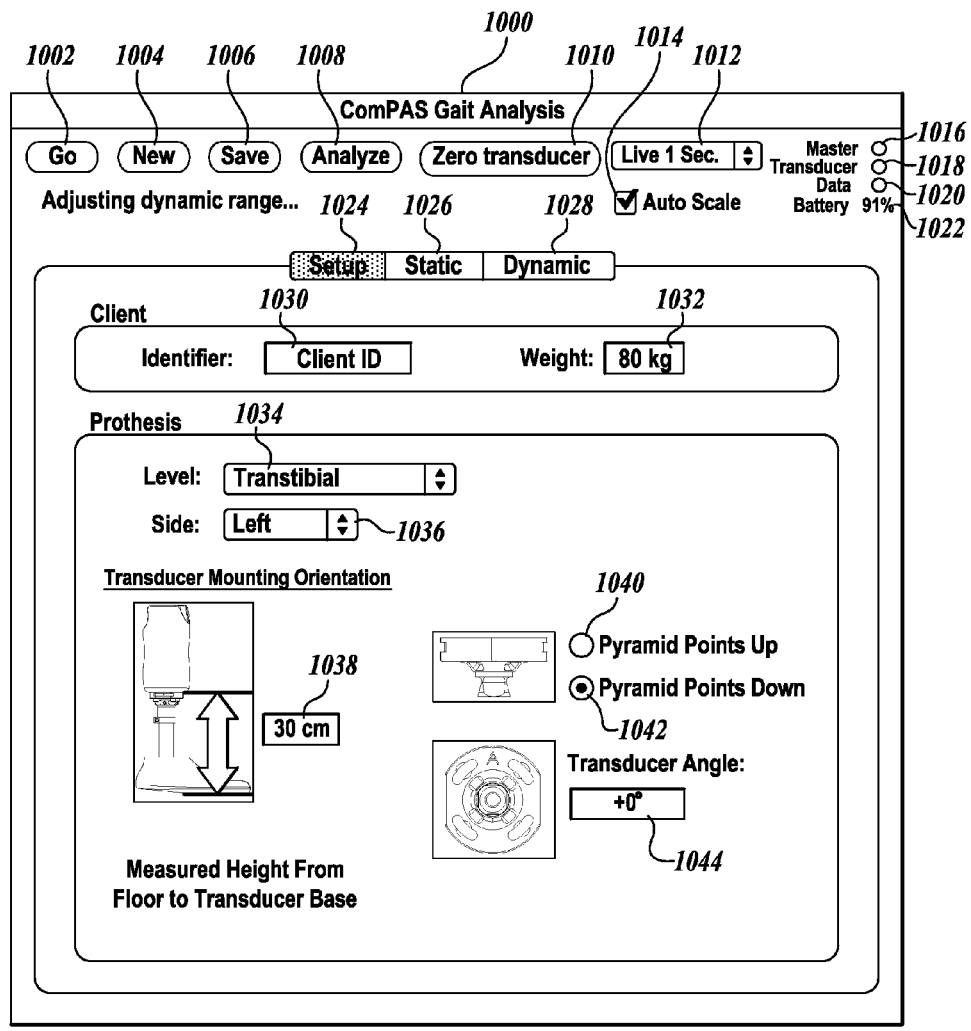
Figure 29:
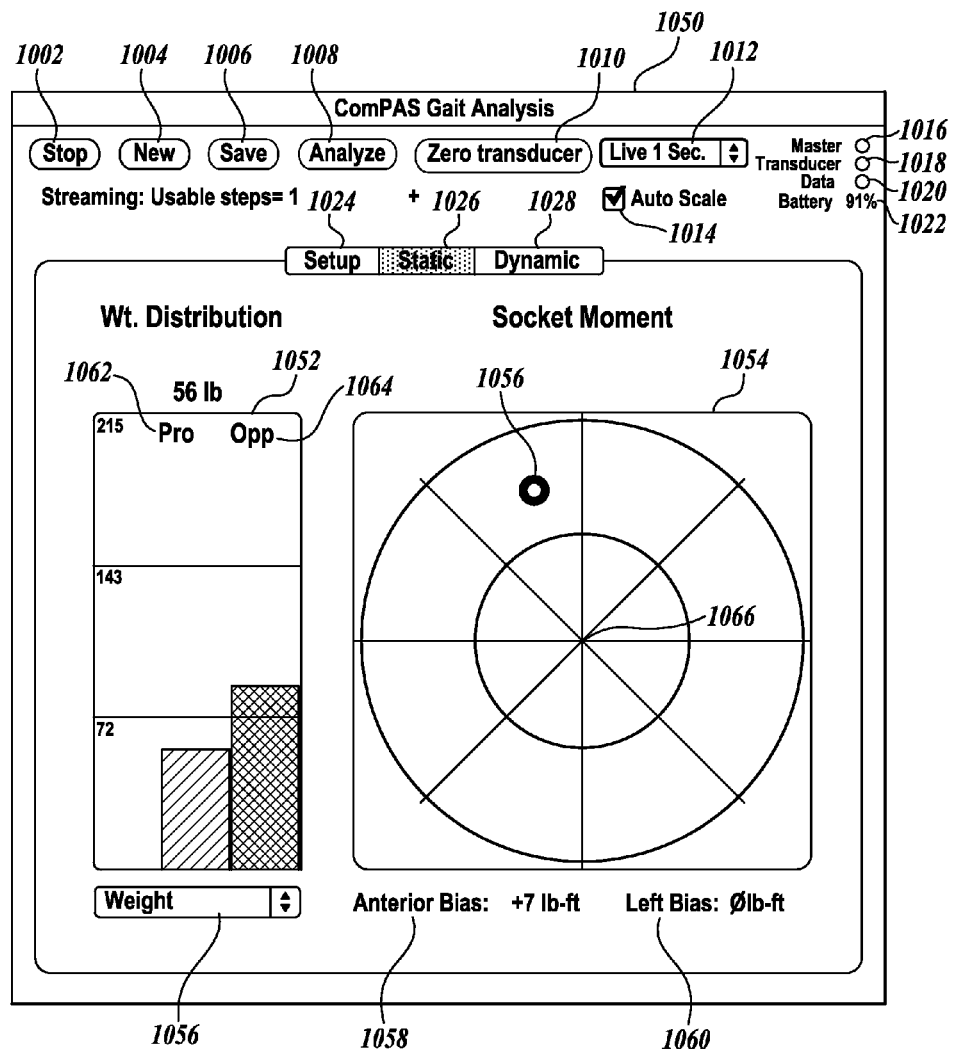
Figure 30:
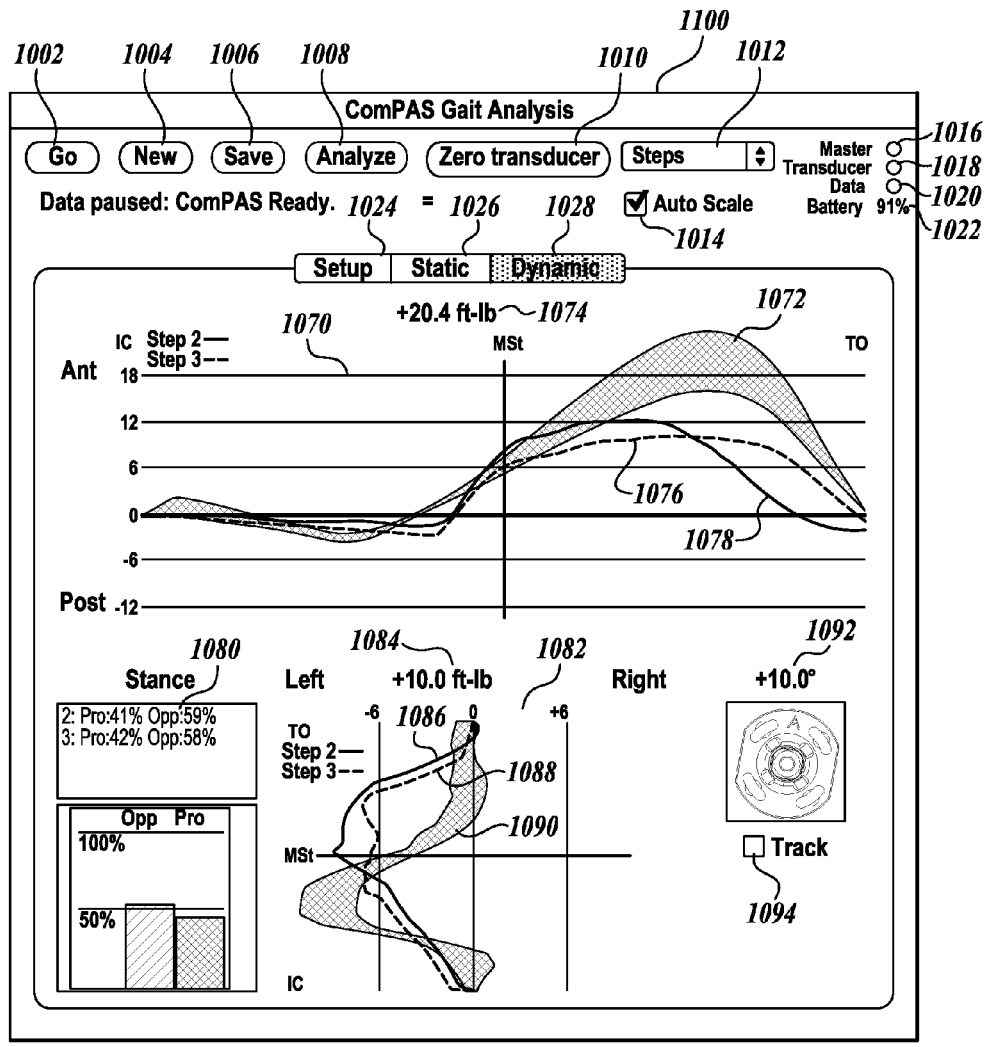

FIGS. 28, 29, and 30 represent an alternative graphical user interface for the gait analysis application 316, including three modes of operation.

FIG. 28 is an illustration of a graphical user interface 1000 for the gait analysis application 316 depicting three modes of operation for the computerized prosthesis alignment system 100. The modes include the setup 1024 mode, static 1026 mode, and dynamic 1028 mode. FIG. 28 illustrates the setup mode 1024. The graphical user interface 1000 includes a "go" button 1002, a "new" button 1004, an "analyze" button 1008, and a "zero transducer" button 1010. In the setup mode 1024, the go button 1002, new button 1004, save button 1006, analyze button 1008, and zero sensor button 1010 are inactive. The graphical user interface 1000 presents to the user 324, a drop down menu 1012 for selecting the rate of updating the data. The graphical user interface 1000 includes a label and check box 1014 for auto scaling. Checking the check box 1014 causes the graphs showing the data in real time to provide a suitable range. The graphical user interface 1000 includes a label and text box 1030 for entering the client ID. The graphical user interface 1000 includes a label and text box 1032 for manually entering the weight of the patient 326. The graphical user interface 1000 includes a label and drop down menu 1034 for entering the level of the amputation. For example, the user 324 may select from the dropdown menu 1034, transtibial or transfemoral. The graphical user interface 1000 includes a label and dropdown menu 1036 for entering whether the prosthesis is a left or right prosthesis. The graphical user interface 1000 includes a label and text box 1038 for manually entering the height of the transducer 104. The graphical user interface 1000 includes a label and a pair of radio buttons 1040 and 1042. The user 324 selects radio button 1040 when the configuration of the inverted pyramid 110 points up. The user 324 selects radio button 1042 when the orientation of the inverted pyramid 110 points down. The graphical user interface 1000 includes a label and text box 1044 for manually entering the transducer angle deviation from a predetermined line of progression. The graphical user interface 1000 includes a status indicator 1016 to monitor the status of the master unit 106, a status indicator 1018 to monitor the status of the transducer 1018, and a status indicator 1020 to monitor whether data is streaming. The graphical user interface 1000 also monitors the battery condition with the battery condition status bar 1022. In the setup mode 1024, the master unit 106 is active but not transmitting; the transducer 104 is in a ready mode; and data streaming is not occurring.

FIG. 29 is an illustration of a graphical user interface 1050 for the static mode 1026 of the computerized prosthesis alignment system 100. In the static mode 1026, the go button 1002 is active, but has been changed into a "stop" button 1002 after its activation. The new button 1004, and the zero transducer button 1010 are active. The save button 1006 and the analyze button 1008 are inactive. The graphical user interface 1000 presents to the user 324, a drop down menu 1012 for selecting the rate of updating the data. The graphical user interface 1000 includes a label and check box 1014 for auto scaling. Checking the check box 1014 causes the graphs showing the data in real time to provide a suitable range. In the static mode 1026, the user 324 is presented with a weight distribution graph 1052 and a socket moment graph 1054. The weight distribution graph 1052 can show the percent of the total weight being supported by the prosthesis 1062 (Pro) and the opposite foot 1064 (Opp), or the user 324 can modify the labels to show the relative percentages of the weight being supported by the prosthesis and opposite leg. The user 324 selects weight in pounds or weight percent by using the dropdown menu 1056.

The socket moment graph 1054 is a chart having a centroid 1066 and a locus 1056 indicating the direction and magnitude of the moments acting on the prosthesis socket 60. The centroid 1066 does not represent the absence of all moment, but rather, the centroid 1066 represents an optimal alignment that may include some amount of anterior/posterior moment and right/left moment acting on the prosthesis socket 60 even when the locus is over the centroid 1066. The socket moment graph 1054 is oriented so that the top correlates to the anterior side of the prosthesis socket 60, the bottom of the graph 1054 correlates to the posterior side of the prosthesis socket 60, the right of the graph 1054 correlates to the right side of the prosthesis socket 60, and the left of the graph 1054 correlates to the left side of the prosthesis socket 60. The object of the socket moment graph 1054 is to allow the user 324 to align the locus 1056 over the centroid 1066 and thus achieve the optimal static alignment. As mentioned before, the centroid 1066 may not correspond with zero moment, but rather an optimal setting that may include some moment in the anterior/posterior plane and also in the right/left plane. Accordingly, because the centroid 1066 may actually represent some moment in both planes, the user 324 may apply an anterior bias 1058 and a left bias 1066 so that the centroid 1066 can actually be placed in the center of the graph 1054 to correspond to the optimal setting even when moments are present in both planes.

Figure 31:
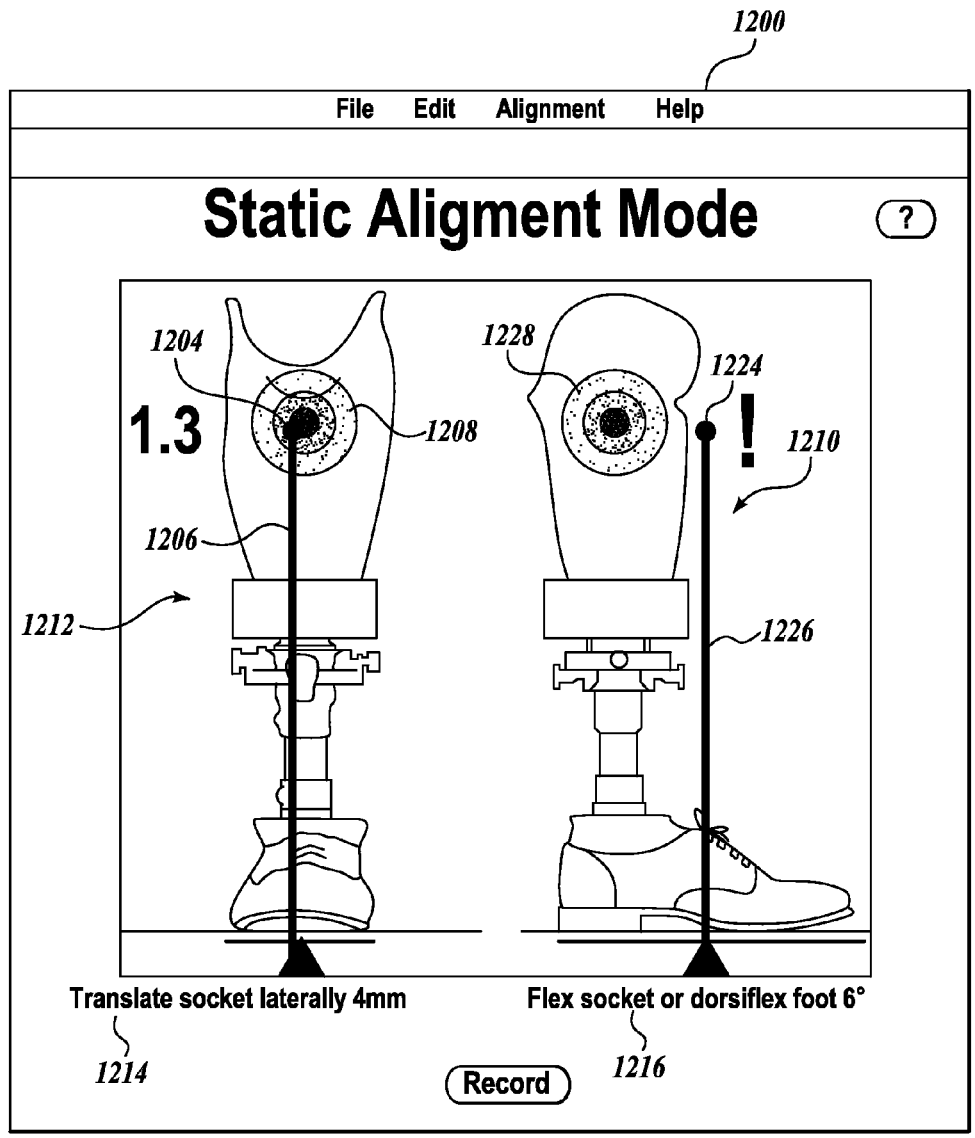

In another embodiment of the static mode, as illustrated in FIG. 31, a graphical user interface 1200 is presented to the user 324 including two graphs representing the anterior/posterior plane 1210, and the right/left plane 1212. Each graph includes a ball 1204, 1224 at the end of a line 1206, 1226 plotted in the center of a target 1208, 1228 that indicates points of balance of moments measured by the transducer 104. The height of the line 1206, 1208 may represent the axial force. When the patient 326 is balanced evenly on each foot, the height of the lines 1206, 1226 should be at the height of the center of the targets 1208, 1228 (half body weight). The displacement of the lines 1206, 1226 to the left or right of the targets 1208, 1228 represents the moment being measured in that plane. The graphical user interface 1200 includes a text dialog box 1214 for the graph 1212, and a text box 1216 for the graph 1210. As the user 324 makes an alignment adjustment that is suggested in the text box below each graph, the balls 1204, 1224 on the lines 1206, 1226 should move toward the targets 1208, 1228. A graphical user interface, as described, may appeal to a user 324 because it presents the information in a manner similar to how they are trained to align a prosthesis. The lines 1208, 1228 are similar to the "load line" commonly used to do bench alignment.

FIG. 30 is an illustration of a graphical user interface 1100 for the dynamic mode 1028 of the computerized prosthesis alignment system 100. In the dynamic mode, the go/stop button 1002, new button 1004, save button 1006, analyze button 1008, and zero transducer button 1010 are active. The save button 1006 and the analyze button become active after selecting the new button 1004. The graphical user interface 1100 includes a dropdown menu 1012 for providing to the user 324, the option of selecting the number of steps to plot. The graphical user interface 1100 includes a label and check box 1014 for auto scaling. Checking the check box 1014 causes the graphs showing the data in real time to provide a suitable range.

In the dynamic mode 1028 of the computerized prosthesis alignment system 100, the graphical user interface 1100 presents to the user 324, a first graph 1070 showing moments in the anterior/posterior plane. The graph 1070 may include plots 1076 and 1078 for various steps selected by the user 324 from the dropdown menu 1012. The graph 1070 includes an optimal moment curve 1072 that includes an upper and a lower limit. The user 324 may make alignment adjustments to fit the step plots within the upper and lower limits of the optimal moment curve 1072. In the dynamic mode 1028 of the computerized prosthesis alignment system 100, the graphical user interface 1100 presents to the user 324, a second graph 1084 showing moment in the right/left plane. The graph 1084 may include plots 1086 and 1088 for various steps selected by the user 324 from the dropdown menu 1012. The graph 1084 includes an optimal moment curve 1090 that includes a right and left limit. The user 324 may make alignment adjustments to fit the step plots within the right and left limits of the optimal moment curve 1090. The graphical user interface 1100 includes the yaw angle 1092 with respect to the predetermined line of progression. The user 324 may select to track the angle or not track the angle by checking or unchecking the checkbox 1094. The graphical user interface 1100 includes a stance chart 1080. The stance chart 1080 may be a bar chart or include text. The stance chart 1080 indicates how much of the weight is being supported by the prosthesis and the opposite foot for the selected steps. For example, in step number 2, the prosthesis supported 41% of the body weight, while the opposite foot supported 59% of the body weight. In step No. 3, the prosthesis supported 42% of the body weight, while the opposite foot supported 58% of the body weight. Algorithms can be used to determine when to start measuring the weight, for example, if the transducer 104 notices the axial force greater than or equivalent to a threshold, the gait analysis application 316 may assume that the stance phase is in progress and then attribute the axial force beginning at the threshold until the axial force diminishes to below a threshold. The weight on the prosthesis is subtracted from the total body weight to calculate the weight on the opposite foot.

Figure 32:
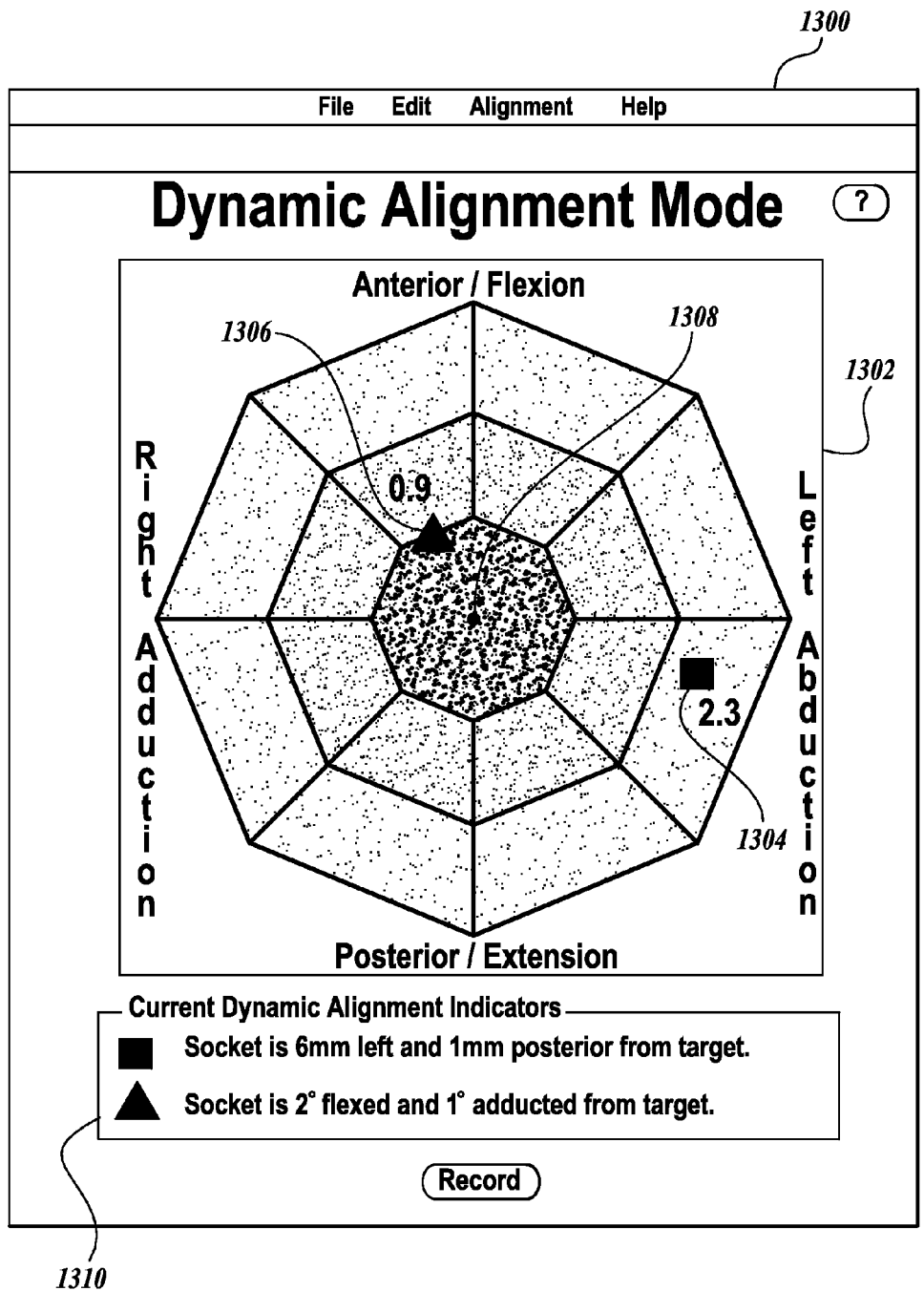

Another embodiment of a graphical user interface 1300 for the dynamic mode is illustrated in FIG. 32. The graphical user interface 1300 presents to the user 324 a coordinate graph system 1302 where a square cursor 1304 represents the translation of the limb, and a triangular cursor 1306 represents the angulation. The center 1308 of the coordinate graph system (the target) represents the ideal alignment. The goal is to move the cursors 1304, 1306 toward the center 1308 based on the text based feedback provided in the text box 1310. Specific alignment feedback may be generated in textual form, such as instructions to the user 324 for angular and translational alignment changes, to bring the prosthesis socket 60 closer to the center 1308 of the coordinate system 1302.

While illustrative embodiments have been illustrated and described, it will be appreciated that various changes can be made therein without departing from the spirit and scope of the invention.

The embodiments of the invention in which an exclusive property or privilege is claimed are defined as follows:

1. A transducer, comprising:
   a transducer body;
   an adaptor on the transducer body for coupling to a prosthesis;
   a beam disposed on each of anterior, posterior, right and left sides of the adaptor, wherein the beams support the adaptor on the transducer body;
   a first strain-measuring device on the transducer to measure forces in a first plane; and
   a second strain-measuring device on the transducer to measure forces in a second plane substantially orthogonal to the first plane;
   wherein the first and the second strain-measuring devices are arranged to reduce measuring forces in a third plane orthogonal to the first and second planes.

2. The transducer of claim 1, wherein the first plane is the anterior/posterior plane, the second plane is the right/left plane, and the third plane is the transverse plane.

3. The transducer of claim 1, comprising third, fourth, fifth, sixth, seventh and eighth strain-measuring devices, wherein a pair of strain-measuring devices is provided on each of the beams on the anterior, posterior, right, and left sides of the adaptor.

4. The transducer of claim 1, further comprising memory to store data.

5. The transducer of claim 1, comprising a first and a second strain gage on a beam on the anterior side of the adaptor, a third and fourth strain gage on a beam on the posterior side of the adaptor, a fifth and sixth strain gage on a beam on the right side of the adaptor, and a seventh and eighth strain gage on a beam on the left side of the adaptor.

6. The transducer of claim 5, wherein two sets of four strain gages is each arranged in a balanced bridge, and each balanced bridge produces a voltage output representative of a moment in a plane.

7. The transducer of claim 6, further comprising a temperature-compensating resistor connected to each bridge, wherein voltage is supplied through the temperature-compensating resistor to each bridge.

8. The transducer of claim 7, further comprising amplification circuits for amplifying the output from the balanced bridges and an analog-to-digital conversion circuit that receives the amplified output from the balanced bridges.

9. The transducer of claim 1, further comprising circuitry to measure the axial load on the transducer.

10. A transducer, comprising:
a transducer body;
an adaptor on the transducer body for coupling to a prosthesis;
a beam disposed on each of the anterior, posterior, right and left sides of the adaptor, wherein the beams support the adaptor to the transducer body, each beam having a strain-measuring device positioned on each of at least two opposite side surfaces of each beam;
a first set of strain-measuring devices configured to measure forces in a first plane; and
a second set of strain-measuring devices configured to measure forces in a second plane substantially orthogonal to the first plane;
wherein the first and the second sets of strain-measuring devices are arranged to reduce measuring forces in a third plane orthogonal to the first and second planes.

11. The transducer of claim 10, wherein the first plane is the anterior/posterior plane, the second plane is the right/left plane, and the third plane is the transverse plane.

12. The transducer of claim 10, further comprising memory to store data.

13. The transducer of claim 10, wherein two sets of four strain gages is each arranged in a balanced bridge, and each balanced bridge produces a voltage output representative of a moment in a plane.

14. The transducer of claim 13, further comprising a temperature-compensating resistor connected to each bridge, wherein voltage is supplied through the temperature-compensating resistor to each bridge.

15. The transducer of claim 14, further comprising amplification circuits for amplifying the output from the balanced bridges and an analog-to-digital conversion circuit that receives the amplified output from the balanced bridges.

16. The transducer of claim 15, further comprising a digital-to-analog conversion circuit connected to the amplification circuit of each balanced bridge to apply an offset voltage to calibrate the output from the amplification circuit.

17. The transducer of claim 10, further comprising circuitry to measure the axial load on the transducer.

18. A transducer, comprising:
a transducer body;
an inverted pyramid adaptor on the transducer body for coupling to a prosthesis;
a first strain-measuring device on the transducer to measure forces in a first plane; and
a second strain-measuring device on the transducer to measure forces in a second plane substantially orthogonal to the first plane;
wherein the first and the second strain-measuring devices are arranged to reduce measuring forces in a third plane orthogonal to the first and second planes.

19. The transducer of claim 18, wherein the first plane is the anterior/posterior plane, the second plane is the right/left plane, and the third plane is the transverse plane.

20. The transducer of claim 18, comprising third, fourth, fifth, sixth, seventh and eighth strain-measuring devices, wherein a pair of strain-measuring devices is provided on each of the anterior, posterior, right, and left sides of the adaptor.

21. The transducer of claim 18, further comprising memory to store data.

22. The transducer of claim 18, comprising a first and a second strain gage on a beam on the anterior side of the adaptor, a third and fourth strain gage on a beam on the posterior side of the adaptor, a fifth and sixth strain gage on a beam on the right side of the adaptor, and a seventh and eighth strain gage on a beam on the left side of the adaptor.

23. The transducer of claim 22, wherein two sets of four strain gages is each arranged in a balanced bridge, and each balanced bridge produces a voltage output representative of a moment in a plane.

24. The transducer of claim 23, further comprising a temperature-compensating resistor connected to each bridge, wherein voltage is supplied through the temperature-compensating resistor to each bridge.

25. The transducer of claim 24, further comprising amplification circuits for amplifying the output from the balanced bridges and an analog-to-digital conversion circuit that receives the amplified output from the balanced bridges.

26. The transducer of claim 25, further comprising a digital-to-analog conversion circuit connected to the amplification circuit of each balanced bridge to apply an offset voltage to calibrate the output from the amplification circuit.

27. The transducer of claim 18, further comprising circuitry to measure the axial load on the transducer.

28. The transducer of claim 8, further comprising a digital-to-analog conversion circuit connected to the amplification circuit of each balanced bridge to apply an offset voltage to calibrate the output from the amplification circuit.

29. The transducer of claim 1, wherein the transducer body comprises a major side forming a surface, the beams rise from the surface and raise the adaptor above the surface.

30. The transducer of claim 10, wherein the transducer body comprises a major side forming a surface, the beams rise from the surface and raise the adaptor above the surface.

31. The transducer of claim 22, wherein the transducer body comprises a major side forming a surface, the beams rise from the surface and raise the adaptor above the surface.

32. The transducer of claim 1, further comprising a hat having a convex spherical surface, the hat is placed over the beams and covers the strain-measuring devices, and the hat is between the adaptor and the transducer body.

33. The transducer of claim 10, further comprising a hat having a convex spherical surface, the hat is placed over the beams and covers the strain-measuring devices, and the hat is between the adaptor and the transducer body.

34. The transducer of claim 22, further comprising a hat having a convex spherical surface, the hat is placed over the beams and covers the strain-measuring devices, and the hat is between the adaptor and the transducer body.

* * * * *

UNITED STATES PATENT AND TRADEMARK OFFICE
CERTIFICATE OF CORRECTION

PATENT NO. : 8,215,186 B2  
APPLICATION NO. : 12/986024  
DATED : July 10, 2012  
INVENTOR(S) : Macomber et al.

Page 1 of 1

It is certified that error appears in the above-identified patent and that said Letters Patent is hereby corrected as shown below:

In the Claims:

| COLUMN | LINE | ERROR |
|---|---|---|
| 27 (Claim 6) | 2 | "gages is each arranged" should read --gages are each arranged-- |
| 27 (Claim 13) | 38 | "gages is each arranged" should read --gages are each arranged-- |
| 28 (Claim 23) | 21 | "gages is each arranged" should read --gages are each arranged-- |

Signed and Sealed this  
Twenty-ninth Day of October, 2013

Teresa Stanek Rea  
*Deputy Director of the United States Patent and Trademark Office*